(12) United States Patent
Shikano et al.

(10) Patent No.: US 9,181,434 B2
(45) Date of Patent: *Nov. 10, 2015

(54) PITUITOUS SILICONE FLUIDS

(75) Inventors: Naoki Shikano, Tokyo (JP); Michael Stephen Starch, Midland, MI (US); Paul Cornelius Vandort, Sanford, MI (US)

(73) Assignees: Dow Corning Corporation, Midland, MI (US); Dow Corning Toray Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/392,573

(22) PCT Filed: Sep. 1, 2010

(86) PCT No.: PCT/US2010/047471
§ 371 (c)(1),
(2), (4) Date: Feb. 27, 2012

(87) PCT Pub. No.: WO2011/028765
PCT Pub. Date: Mar. 10, 2011

(65) Prior Publication Data
US 2012/0156148 A1    Jun. 21, 2012

Related U.S. Application Data

(60) Provisional application No. 61/239,529, filed on Sep. 3, 2009.

(51) Int. Cl.
| | |
|---|---|
| C08L 83/10 | (2006.01) |
| A61K 8/891 | (2006.01) |
| A61K 8/894 | (2006.01) |
| A61Q 19/00 | (2006.01) |
| C08L 83/14 | (2006.01) |
| A61Q 1/02 | (2006.01) |
| A61Q 5/12 | (2006.01) |
| A61Q 17/04 | (2006.01) |

(52) U.S. Cl.
CPC ............... *C08L 83/10* (2013.01); *A61K 8/891* (2013.01); *A61K 8/894* (2013.01); *A61Q 19/00* (2013.01); *C08L 83/14* (2013.01); *A61Q 1/02* (2013.01); *A61Q 5/12* (2013.01); *A61Q 17/04* (2013.01)

(58) Field of Classification Search
CPC ........................................................ A61K 8/89
See application file for complete search history.

(56) References Cited

U.S. PATENT DOCUMENTS

| | | | | |
|---|---|---|---|---|
| 5,573,709 | A * | 11/1996 | Wells | 510/122 |
| 5,880,210 | A * | 3/1999 | Schulz et al. | 524/731 |
| 6,239,378 | B1 * | 5/2001 | Shephard | 174/110 S |
| 2002/0061998 | A1 | 5/2002 | Cray et al. | |
| 2006/0270789 | A1 * | 11/2006 | Osawa | 524/837 |
| 2007/0167563 | A1 * | 7/2007 | Cray et al. | 524/588 |
| 2008/0292574 | A1 | 11/2008 | Uehara | |
| 2010/0303743 | A1 | 12/2010 | Garaud et al. | |

FOREIGN PATENT DOCUMENTS

| | | |
|---|---|---|
| EP | 0922734 | 6/1999 |
| EP | 1070734 A2 * | 1/2001 |
| WO | 2004058858 | 7/2004 |
| WO | 2006045418 | 5/2006 |
| WO | 2006106362 | 10/2006 |
| WO | WO 2007109240 A2 * | 9/2007 |
| WO | WO 2007109260 A2 * | 9/2007 |
| WO | WO 2007109282 A2 * | 9/2007 |

* cited by examiner

*Primary Examiner* — Sean Basquill
*Assistant Examiner* — Mark V Stevens
(74) *Attorney, Agent, or Firm* — Warner Norcross & Judd LLP

(57) ABSTRACT

Personal care compositions containing pituitous silicone fluids compositions are disclosed. The silicone fluid compositions contain certain branched and/or high molecular weight organopolysiloxanes that demonstrate pituitous rheological behavior. When formulated into personal care compositions, the silicone fluids provide enhanced sensory and film-forming properties based on their pituitous rheological properties.

19 Claims, 7 Drawing Sheets

Normal Force Measurements for Various Linear PDMS fluid compositions
as detailed in Example 1

Normal Force Measurements for Various VBS fluid compositions as detailed in Example 1

Normal Force Measurements for Various T and Q branched silicone fluid compositions as detailed in Example 3

Normal Force Measurements for Branched silicone fluid compositions
as detailed in Example 4

Normal Force Measurements for Branched silicone fluids
as detailed in Example 4

Normal Force Measurements for Branched silicone fluids
as detailed in Example 6

Normal Force Measurements for Branched silicone fluids
as detailed in Example 7B

PITUITOUS SILICONE FLUIDS

CROSS REFERENCE TO RELATED APPLICATIONS

This application is a U.S. national stage filing under 35 U.S.C. §371 of PCT Application No. PCT/US10/047471 filed on Sep. 1, 2010, currently pending, which claims the benefit of U.S. Provisional Patent Application No. 61/239,529 filed Sep. 3, 2009 under 35 U.S.C. §119 (e). PCT Application No. PCT/US10/047471 and U.S. Provisional Patent Application No. 61/239,529 are hereby incorporated by reference.

TECHNICAL FIELD

Figure 1:
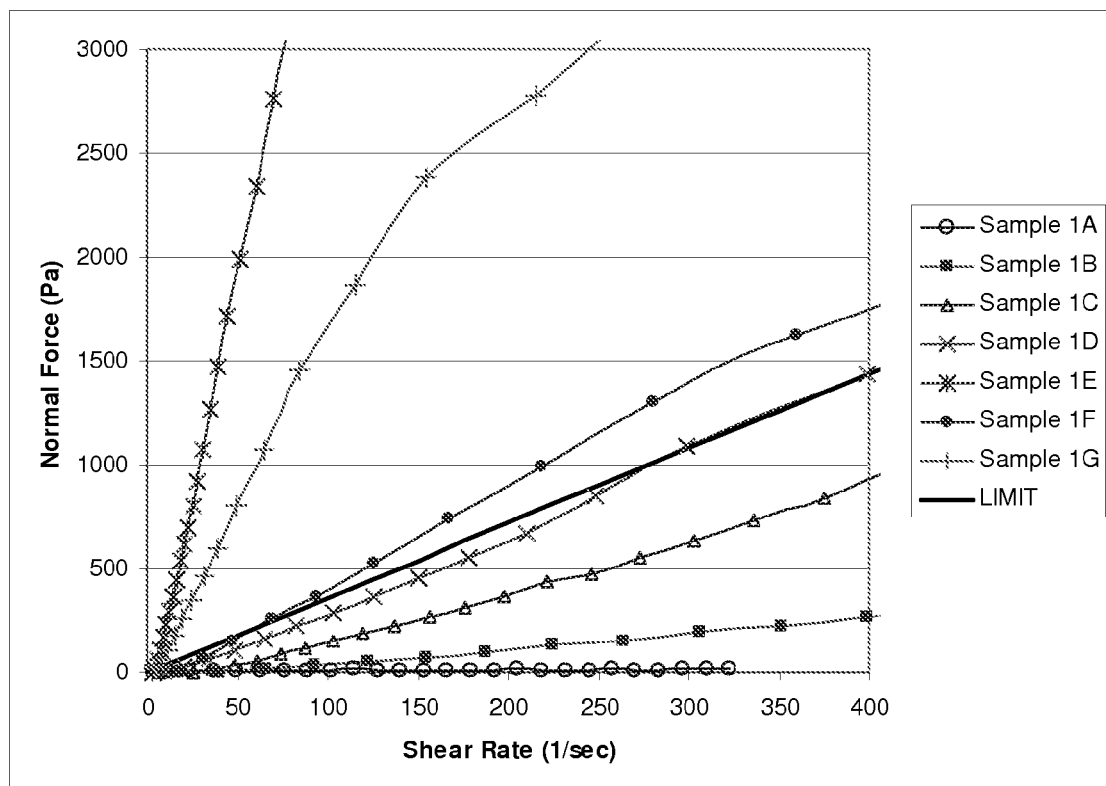
FIG. 1—Normal Force Measurements for Various Linear PDMS fluid compositions as detailed in Example 1

This disclosure relates to personal care compositions containing pituitous silicone fluids. The silicone fluid compositions contain certain branched and/or high molecular weight organopolysiloxanes that demonstrate pituitous rheological behavior. When formulated into personal care compositions, the silicone fluids provide enhanced sensory and film-forming properties based on their pituitous rheological properties.

BACKGROUND

Silicone fluids are widely used in various personal care compositions. The most common silicone fluids used are dimethyl siloxane fluids, which are typically either low molecular weight cyclic molecules of linear polymers. Polydimethylsiloxane (PDMS) is a linear polymer that is available in a wide range of molecular weights. The viscosity of PDMS increases with molecular weight. When the molecular weight of the PDMS is large enough to exhibit a viscosity in excess of 600,000 centipoise (cP), the fluids are more easily handled when dispersed in a suitable solvent (e.g. low viscosity PDMS fluids, cyclic dimethyl siloxanes, or hydrocarbon solvents). In this way PDMS with a viscosity of several million cP can be easily incorporated into various skin care compositions. In a similar manner, high molecular weight organopolysiloxane resins and elastomers can be incorporated into personal care compositions by first dispersing them in a suitable solvent.

Besides providing certain functional benefits, silicones are incorporated into personal care products for their inherent aesthetic benefits. In particular, formulators will optimize the overall aesthetics of personal care products by selecting certain types and amounts of a silicone. As such, there is a continuing need in this industry to discover new silicone compositions that provide improved product aesthetics, sensory perceptions, or functional improvements. The present inventors have discovered certain silicone fluid compositions that provide such improvements.

SUMMARY

The present inventors have discovered that silicone fluid compositions having pituitous rheological properties provide personal care products with enhanced aesthetic and sensory properties. Furthermore, the disclosed pituitous silicone fluid compositions may provide enhanced film formation of various personal care actives upon application to skin. For example, the SPF performance of sunscreens may be enhanced when delivered with the pituitous silicone fluid compositions of the present disclosure.

Pituitous fluids are fluids that display particular types of rheological behavior. The most easily recognized rheological behavior for the pituitous fluids is their "stringing" behavior, which is the formation of thin strings or threads when a small amount of the pituitous fluid is separated from the bulk of the fluid. Another rheological characteristic exhibited by pituitous fluids is that they develop a normal force when subjected to shear stress. When a pituitous fluid is subjected to shear stress in the x-y plane, a force is developed in the z direction (perpendicular, or "normal" to the plane of shear). This behavior is related to a phenomenon known as the Weissenberg Effect whereby polymers in solution that are stirred tend to climb up the stirrer due to entanglements between polymer chains that develop under shear stress. Using a controlled stress rheometer, the normal force may be measured.

The pituitous silicone fluids of this disclosure are often highly lubricious yet form very persistent films on surfaces. As the pituitous fluids are sheared, the normal force developed resists thinning of the fluid and thereby maintaining a thicker lubrication layer between the moving surfaces. We have found that that certain branched and high molecular weight silicone fluids exhibit novel sensory and film-forming properties and these properties correlate with pituitous rheological behavior. We have found that these pituitous fluids provide benefits that cannot be achieved with most straight chain PDMS fluids or crosslinked PDMS materials such as silicone elastomers for example such as those disclosed in U.S. Pat. No. 5,654,362.

DETAILED DESCRIPTION

This disclosure provides personal care compositions containing a silicone fluid having pituitous rheological properties. As used herein, "pituitous" refers to the rheological property of an increasing normal force (typically measured in Pascals) observed in the perpendicular direction when a constantly increasing shear (typically measured in sec$^{-1}$) is applied to a film or layer of the fluid. In other words, when a pituitous fluid is subjected to shear stress in the x-y plane, a force is developed in the z direction (perpendicular or normal to the plane of shear). Pituitous rheology of the present silicone fluids may be measured using a controlled stress rheometer. Such rheometers are commercially available, such as TA Instruments AR 1000-N (109 Lukens Drive, New Castle Del. 19720). The fluid is held between a flat disk (attached to the rheometer) and a stationary plate equipped with a load cell. A controlled amount of force (torque) is applied to the shaft attached to the disc thus subjecting the sample to a shear stress. Typically, the torque is increased during the experiment and the disc rotates at an increasing rate which is recorded as the shear rate. As the fluid sample is being subjected to the shear stress, the normal force is recorded by the load cell. The results of the evaluations of the silicone fluid rheological properties using such instruments are reported as a plot of normal force in Pascals vs a perpendicular shear rate in $\sec^{-1}$.

The silicone fluids useful in the personal care compositions of the present disclosure possess rheological properties such that when a plot of normal force in Pascal vs a perpendicular shear rate in $\sec^{-1}$ is measured using a controlled stress rheometer as described above, the plot has an average slope that is greater than 3.6.

The pituitous silicone fluids of the present disclosure contain an organopolysiloxane or mixture of organopolysiloxanes and optionally a carrier fluid.

Organopolysiloxanes are polymers containing siloxy units independently selected from $(R_3SiO_{1/2})$, $(R_2SiO_{2/2})$, $(RSiO_{3/2})$, or $(SiO_{4/2})$ siloxy units, where R is typically an organo or hydrocarbon group. The siloxy units are commonly referred to as M, D, T, and Q units respectively. The structural formula for each of these units is shown below.

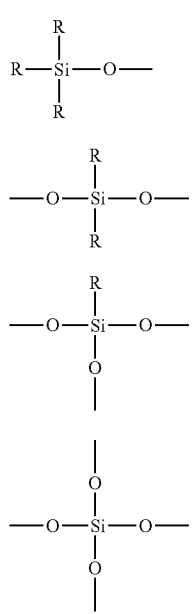

These siloxy units can be combined in various manners to form cyclic, linear, or branched structures. The chemical and physical properties of the resulting polymeric structures will vary depending on the number and type of siloxy groups present in the organopolysiloxane. For example organopolysiloxanes can be volatile fluids, low viscosity fluids, high viscosity fluids/gums, elastomers, rubbers, or resins.

The organopolysiloxanes useful in the personal care compositions of the present disclosure are those that provide pituitous rheological properties to the silicone fluid compositions. As such, the organopolysiloxane may contain a variety of M, D, T, or Q siloxy units. Typically, sufficient D, T, or Q units are present in the organopolysiloxane to obtain certain high molecular weights and/or branching so as to possess pituitous rheological properties alone (neat), or when used in combination with other carrier fluids (described below), to provide the resulting silicone fluid composition with pituitous rheological properties.

In one embodiment, the organopolysiloxane selected as a component in the present pituitous silicone fluid composition is a polydiorganosiloxane gum. As used herein, polydiorganosiloxane gums are organopolysiloxanes comprising predominately D siloxy units and are of sufficient molecular weight to impart pituitous behavior to the silicone compositions. Alternatively, the polydiorganosiloxane gum is of sufficient molecular weight to impart a viscosity of at least 1,000,000 mm$^2$/s at 25° C., or alternatively 2,000,000 mm$^2$/s at 25° C. Alternatively, the molecular weight of the diorganopolysiloxane gum is sufficient to impart a Williams plasticity number of at least 40 as determined by the American Society for Testing and Materials (ASTM) test method 926. Typically, the plasticity number should be 40 to 200, or alternatively 50 to 150. Alternatively, the molecular weight of the diorganopolysiloxane gum is at least 600,000 Daltons, or alternatively at least 1,000,000 Daltons, or alternatively at least 2,000,000 Daltons.

The silicon-bonded organic groups of the diorganopolysiloxane may be independently selected from hydrocarbon, or halogenated hydrocarbon groups. The hydrocarbon groups may be specifically exemplified by alkyl groups having 1 to 20 carbon atoms, such as methyl, ethyl, propyl, butyl, pentyl and hexyl; cycloalkyl groups, such as cyclohexyl and cycloheptyl; aryl groups having 6 to 12 carbon atoms, such as phenyl, tolyl and xylyl; aralkyl groups having 7 to 20 carbon atoms, such as benzyl and phenylethyl. The hydrocarbon group may also be an alkenyl group having 2 to 20 carbon atoms exemplified by vinyl, allyl, butenyl, pentenyl, hexenyl and decenyl, preferably vinyl or hexenyl groups. The halogenated alkyl groups may have 1 to 20 carbon atoms, such as 3,3,3-trifluoropropyl and chloromethyl.

The diorganopolysiloxane may be endblocked with any of the organic groups as described above, or alternatively may be silanol (hydroxy) endblocked.

The polydiorganosiloxane can be a homopolymer, a copolymer or a terpolymer containing such organic groups. Examples include copolymers comprising dimethylsiloxy units and phenylmethylsiloxy units, copolymers comprising dimethylsiloxy units and 3,3,3-trifluoropropylmethylsiloxy units, copolymers of dimethylsiloxy units and diphenylsiloxy units and interpolymers of dimethylsiloxy units, diphenylsiloxy units and phenylmethylsiloxy units, among others. The molecular structure is also not critical and is exemplified by straight-chain and partially branched straight-chain structures, the linear systems being the most typical.

Specific illustrations of diorganopolysiloxane gums include: trimethylsiloxy-endblocked dimethylsiloxane, trimethylsiloxy-endblocked dimethylsiloxane-methylvinylsiloxane copolymers; trimethylsiloxy-endblocked methylphenylsiloxane-dimethylsiloxane-methylvinylsiloxane copolymers; trimethylsiloxy-endblocked 3,3,3-trifluoropropylmethyl siloxane copolymers; trimethylsiloxy-endblocked 3,3,3-trifluoropropylmethyl-methylvinylsiloxane copolymers; dimethylvinylsiloxy-endblocked dimethylpolysiloxanes; dimethylvinylsiloxy-endblocked dimethylsiloxane-methylvinylsiloxane copolymers; dimethylvinylsiloxy-endblocked methylphenylpolysiloxanes; dimethylvinylsiloxy-endblocked methylphenylsiloxane-dimethylsiloxane-methylvinylsiloxane copolymers; and similar copolymers wherein at least one end group is dimethylhydroxysiloxy.

The diorganopolysiloxane gum may also consist of combinations of two or more organopolysiloxanes.

Methods for preparing diorganopolysiloxane gums are well known and many are commercially available. Representative commercial products suitable in the present silicone compositions include; Dow Corning® SGM-36 Gum and SGM-3 Gum.

The diorganopolysiloxane gum is dispersed in the carrier fluid (as described below) to form the pituitous silicone fluid compositions. The concentration of the diorganopolysiloxane gum in the carrier fluid may vary. The amount of the diorganopolysiloxane gum dispersed in the carrier fluid should be an amount sufficient to impart pituitous behavior. However, typically the concentration of the diorganopolysiloxane will be 10 to 50 weight percent, alternatively 15 to 35 weight percent. This amount will vary depending on the molecular weight of the diorganopolysiloxane gum. Typically at least 20 weight percent of the gum is used when the molecular weight of the gum is 650,000 Daltons, or alternatively at least 14 weight percent when the molecular weight of the diorganopolysiloxane is 2,000,000 Daltons.

In another embodiment, the organopolysiloxane selected as a component in the present pituitous silicone fluid composition is a Q branched organopolysiloxane. In one aspect of this embodiment, the Q branched organopolysiloxane is selected from the branched siloxanes as disclosed in U.S. Pat. No. 6,806,339.

A branched siloxane according to this aspect of the present disclosure contains:

i) one or more Q units of the formula ($SiO_{4/2}$) and ii) from 15 to 995 D units of the formula $R^b{}_2SiO_{2/2}$ which units (i) and (ii) may be inter-linked in any appropriate combination, and iii) M units of the formula $R^a R^b{}_2 SiO_{1/2}$, wherein each $R^a$ substituent is selected from the group consisting of an alkyl group having from 1 to 6 carbon atoms, an alkenyl group having from 2 to 6 carbon atoms and an alkynyl group having from 2 to 6 carbon atoms, at least three Ra substituents in the branched siloxane being alkenyl or alkynyl units, and each $R^b$ substituent is selected from the group consisting of an alkyl group having from 1 to 6 carbon atoms, an alkenyl group having 2 to 6 carbon atoms, an aryl group, an alkoxy group, an acrylate group and a methacrylate group.

Typically the aliphatically unsaturated hydrocarbon groups are either alkenyl or alkynyl groups. Typically at least 50% of $R^a$ substituents are alkenyl groups. Each alkenyl group may be selected from vinyl, allyl, butenyl, pentenyl and hexenyl groups but is typically selected from a vinyl (vi) and a hexenyl (hex) group.

The branched siloxane comprises at least one Q unit bonded to four $(R^b{}_2SiO_{2/2})n$ chains and for example can have the formula

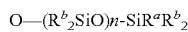

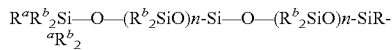

where each n is independently from 1 to 500. The $R^b$ substituent is an alkyl groups for example, a methyl, ethyl, propyl, isopropyl, butyl, pentyl or hexyl group; but typically is a methyl group.

Hence, in the case when there is only a single unit of the formula $SiO_{4/2}$ present in the branched siloxane, the branched siloxane may have substantially the following formula wherein each n is independently from 1 to 500, alternatively n is 95-500, or alternatively 250-300.

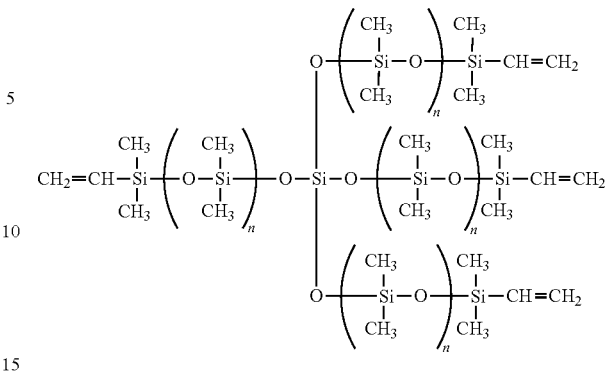

In another embodiment, the organopolysiloxane used in the pituitous silicone fluid compositions is a T or Q branched organopolysiloxane having a high MW, such as the organopolysiloxanes prepared by the techniques as taught in WO2006/106362, which is incorporated herein by reference. Thus, the organopolysiloxane may be obtained by;

i) preparing an organopolysiloxane containing polymer by the polycondensation of siloxane containing monomers and/or oligomers which comprise condensable groups in the presence of an organopolysiloxane and/or an organic based diluent material, a suitable catalyst and optionally an end-blocking agent; and ii) where required quenching the polymerization process; wherein the diluent material is substantially retained within the resulting diluted organopolysiloxane.

An organosiloxane containing polymer is intended to mean a polymer comprising multiple organopolysiloxane groups per molecule and is intended to include a polymer substantially containing only organopolysiloxane groups in the polymer chain or polymers where the backbone contains both organopolysiloxane groups and e.g. organic polymeric groups in chain.

Polycondensation (otherwise known as condensation polymerization) is the polymerization of multiple monomers and/or oligomers with the elimination of low molecular weight by-product(s) such as water, ammonia or methanol etc.).

Polycondensation type polymerization reactions are most generally linked to the interaction of compounds having hydroxyl and/or hydrolysable end groups which can interact with the release of e.g. water or methanol or the like.

Thus, the T or Q branched organopolysiloxane may be obtained by condensation polymerization of i) a polyorganosiloxane having at least one hydroxyl group capable of undergoing condensation polymerization, ii) an alkoxysilane of the formula $R'Si(OR^4)_3$ or $Si(OR^4)_4$ in the presence of at least one hydrocarbon solvent or silicone fluid; wherein polymerization is facilitated by addition of at least one condensation catalyst and by maintaining the mixture at a temperature of from 30° C. to 110° C.

The polyorganosiloxane i) may be linear, substantially linear, or branched. In some aspects, linear or substantially linear low molecular weight/low viscosity polyorganosiloxanes having reactive hydroxyl groups are used as starting materials for condensation polymerization. For example, such polyorganosiloxanes can be generally characterized by formula (1):

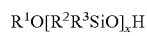 (1)

wherein each R is independently selected from a hydrogen atom, an alkyl or substituted alkyl group containing 1 to 8 carbon atoms, an aryl or substituted aryl group containing 1 to 8 carbon atoms, and wherein x is an integer with a value of at least 2. In certain aspects, x is an integer with a value range of 2-500. In other aspects, x is an integer with a value range of 3-100. In additional aspects, x is an integer with a value range of 50-80. Examples of R include, but are not limited to, methyl, ethyl, propyl, isopropyl, butyl, sec-butyl, iso-butyl, tert-butyl, perfluorobutylethyl, phenyl ethyl, chloropropyl, fluoropropyl, vinyl, and phenyl.

The alkoxysilane ii) may be either a trialkoxysilane or tetraalkoxysilane having the $R'Si(OR^4)_3$ or $Si(OR^4)_4$ respectively. R' may be an organic group, alternatively a hydrocarbon, or alternatively an alkyl group. $R^4$ is a C1 to C4 alkyl group. Representative non limiting examples of trialkoxysilanes useful in this embodiment include methyltrimethoxysilane, ethyltrimethoxysilane, octyltrimethoxysilane, and corresponding ethoxy silanes. Representative non limiting examples of tetraalkoxysilanes include tetramethoxysilane, and tetraethoxysilane (TEOS).

The amounts of components i) and ii) used in the condensation reaction may vary. In particular the amount of alkoxysilane added is such as to provide sufficient branching in the resulting organopolysiloxane to provide pituitous rheology. Typically the weight ratio of i) to ii) varies from 100/1 to 10/1.

Any suitable condensation polymerization reaction pathway may be utilized for formation of the silicone polymer. Similarly, any suitable condensation catalyst known in the art may be mixed with the siloxane starting materials to facilitate polymerization. In certain aspects, protic acids, Lewis acids and bases, organic acids and bases, and inorganic acids and bases are used. For example, $BF_3$, $FeCl_3$, $AlCl_3$, $ZnCl_2$, and $ZnBr_2$ can be used. Alternatively, organic acids such as those having the general formula $RSO_3H$, wherein R represents an alkyl group having from 6 to 18 carbon atoms (for example, a hexyl or dodecyl group), an aryl group (for example, a phenyl group), or an alkaryl group (for example, dodecylbenzyl) can be used. Other condensation-specific catalysts include, but are not limited to, n-hexylamine, tetramethylguanidine, carboxylates of rubidium or cesium, hydroxides of potassium, sodium, magnesium, calcium or strontium, and phosphonitrile halide ion-based catalysts having the general formula $[X(PX_2\!=\!N)_z PX_3]^+$, wherein X denotes a halogen atom and wherein z is an integer from 1 to 6. In certain aspects, $[PCl_3\!=\!N\!-\!PCl_2\!=\!N\!-\!PCl_3]^+ PCl_6^-$ is the catalyst used.

Typically the amount of catalyst present is from 2 ppm to 300 ppm (by weight, based on weight of the polyorganosiloxane.

One of skill in the art will appreciate that condensation polymerization involves the production of water as a by-product. In certain aspects of the invention, it may or may not be necessary to remove the water formed during condensation. In some aspects, removal of water is required and is done during or after condensation polymerization but before neutralization. Methods of removing water are known in the art.

In certain aspects, the catalyst(s) chosen, desired reaction products and their properties, as well as the presence of optional end-blocking agent and/or other optional additives, may affect how reaction temperature is chosen. In some aspects, condensation polymerization is carried out at a temperature of from 30° C. to 110° C.

In another embodiment, the organopolysiloxane used in the pituitous silicone fluid compositions is a highly branched organopolysiloxane from the reaction of;
A) an organohydrogensiloxane having at least two SiH containing cyclosiloxane rings in its molecule
B) a compound or mixture of compounds having at least two aliphatic unsaturated hydrocarbon groups in its molecule,
C) a hydrosilylation catalyst, and
D) optionally, a compound or mixture of compounds having a mono terminal aliphatic unsaturated hydrocarbon group.

Highly branched organopolysiloxanes that are particularly useful to prepare the pituitous silicone fluid compositions of the present disclosure are those as described in U.S. Pat. No. 7,432,338, U.S. Pat. No. 7,429,636, and U.S. Pat. No. 7,378,482, which are hereby incorporated herein by reference.

Component (A) used to prepare the highly branched organopolysiloxane of the present disclosure is an organohydrogensiloxane having at least two SiH containing cyclosiloxane rings in its molecule. The cyclosiloxane rings of A) the organohydrogensiloxane are linked together by a divalent organic or siloxane group, or combination thereof. The divalent linking group may be designated as Y and the cyclosiloxane as G. Thus, the organohydrogensiloxane of the present invention may be represented by the general formula $G\text{-}[Y\text{-}G]_a$, where G is a cyclosiloxane as described above and Y is a divalent organic, a siloxane, a polyoxyalkylene group, or combination thereof, and the subscript a is greater than zero.

When Y is a divalent organic, it may be a divalent hydrocarbon containing 1 to 30 carbons, either as aliphatic or aromatic structures, and may be branched or un-branched. Alternatively, Y can be an alkylene group containing 2 to 20 carbons, or alternatively containing 4 to 12 carbons.

When Y is a divalent organic, it may also be selected from an organic polymer, such as a polyoxyalkylene group.

When Y is a siloxane group it may be selected from any organopolysiloxane containing at least two divalent hydrocarbon groups, designated as $R^5$. Thus, the siloxane linking group can be any organopolysiloxane comprising at least two siloxane units represented by the average formula $R^5_m SiO_{(4-m)/2}$ wherein
R is an organic group,
$R^5$ is a divalent hydrocarbon, and
m is zero to 3

The $R^5$ group may be present on any mono, di, or tri-siloxy unit in an organopolysiloxane molecule, for example; $(R^5R_2SiO_{0.5})$, $(R^5RSiO)$, or $(R^5SiO_{1.5})$, as well as in combination with other siloxy units not containing an $R^5$ substituent, such as $(R_3SiO_{0.5})$, $(R_2SiO)$, $(RSiO_{1.5})$, or $(SiO_2)$ siloxy units where R is independently any organic group providing there are at least two $R^5$ substituents in the organopolysiloxane. Representative $R^5$ groups include; ethylene, propylene, butylene, isobutylene, hexylene, and similar homologs. Alternatively, $R^5$ is ethylene.

Representative, non-limiting, examples of such siloxane based structures suitable as siloxane linking groups include;

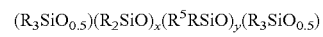

where $x \geq 0$, $y \geq 2$, and z is $\geq 0$

Organohydrogensiloxane having at least two SiH containing cyclosiloxane rings (component A) may be prepared via a hydrosilylation reaction of
a) an organohydrogencyclosiloxane having at least two SiH units on the siloxane ring and,
b) a compound or mixture of compounds having at least two aliphatic unsaturated groups in its molecule.

The organohydrogencyclosiloxane (a) having at least two SiH units on the siloxane ring may contain any number of siloxy units (as defined above) provided there are at least two SiH units on the cyclosiloxane ring. For example, the cyclic siloxane can comprise any number of M, $M^H$, D, $D^H$, or $T^H$ siloxy units. Representative, non-limiting examples of such organohydrogencyclosiloxanes useful to prepare component (A) have the average formula $D^H_a D_b$ where a is ≥1 and b is ≥0, and a+b≥3. Alternatively, the organohydrogencyclosiloxane may be selected from those having the formula $[(CH_3)HSiO]_g$ where g is 3-8, such as $D^H_4$, $D^H_5$, $D^H_6$, or mixtures thereof.

Suitable compounds containing at least two aliphatic unsaturated hydrocarbon groups in its molecule are described below as component B).

Hydrosilylation reactions involving organohydrogensiloxanes and unsaturated compounds are well known. Any suitable hydrosilylation catalysts know in the art may be used, or alternatively may be selected from those described below as component C). Any of the known hydrosilylation techniques and reactions may be employed to prepare component A) from i) organohydrogencyclosiloxane having at least two SiH units on the siloxane ring and, B) a compound or mixture of compounds having at least two aliphatic unsaturated groups in its molecule. However, the reaction is conducted in such a manner to provide an organohydrogensiloxane having at least two SiH containing cyclosiloxane rings in its molecule.

Thus, component A of the present disclosure contains at least two silicon-bonded hydrogen atom per molecule, alternatively at least 4 silicon-bonded hydrogen atoms per molecule, or alternatively at least 6 silicon-bonded hydrogen atoms per molecule. This can be accomplished by using in the hydrosilylation reaction a molar excess of the a) the organohydrogencyclosiloxane having at least two SiH units on the siloxane ring vs. the compound containing at least two aliphatic unsaturated groups in its molecule. The molar excess may be expressed as the molar ratio of SiH units to unsaturated group, such ratio may range from 2/1 to 8/1, alternatively from 2/1 to 6/1, or alternatively from 3/1 to 4/1.

Alternatively, the organohydrogensiloxane useful as component A) may be selected from any of the organohydrogensiloxanes taught in WO03/093349, which is herein incorporated by reference for its teaching of suitable organohydrogensiloxanes.

Component (B) used to prepare the highly branched organopolysiloxane of the present disclosure is a compound, or any mixture of compounds, containing at least two aliphatic unsaturated groups in its molecule. The compound may be any diene, diyne or ene-yne compound. Diene, diyne or ene-yne compounds are those compounds (including polymeric compounds) wherein there are at least two aliphatic unsaturated groups with some separation between the groups within the molecule. Typically, the unsaturation groups are at the termini of the compound, or pendant if part of a polymeric compound. Compounds containing terminal or pendant unsaturated groups can be represented by the formula $R^6$—Y—$R^6$ where $R^6$ is a monovalent unsaturated aliphatic hydrocarbon group containing 2 to 12 carbon atoms, and Y is a divalent organic or siloxane group or a combination of these. Typically $R^6$ is $CH_2$=CH—, $CH_2$=CHCH$_2$—, $CH_2$=CH(CH$_2$)$_4$—, $CH_2$=C(CH$_3$)CH$_2$— or CH≡C—, and similar substituted unsaturated groups such as $H_2C$=C(CH$_3$)—, and HC≡C(CH$_3$)—.

The compound having the formula $R^6$—Y—$R^6$ as component B) may be considered as being a "organic", "hydrocarbon", "organic polymer", "polyether" or "siloxane", or combinations thereof, depending on the selection of Y. Y may be a divalent hydrocarbon, a siloxane, a polyoxyalkylene, a polyalkylene, a polyisoalkylene, a hydrocarbon-silicone copolymer, or mixtures thereof.

In one embodiment, the component (B) is selected from an organic compound, herein denoted as ($B^1$), having the formula $R^6$—$Y^1$—$R^6$ where $R^6$ is a monovalent unsaturated aliphatic group containing 2 to 12 carbon atoms and $Y^1$ is a divalent hydrocarbon. The divalent hydrocarbon $Y^1$ may contain 1 to 30 carbons, either as aliphatic or aromatic structures, and may be branched or un-branched. Alternatively, the linking group $Y^1$ in $B^1$ may be an alkylene group containing 1 to 12 carbons. Component ($B^1$) may be selected from α, ω-unsaturated alkenes or alkynes containing 1 to 30 carbons, and mixtures thereof. Component ($B^1$) may be exemplified by, but not limited to 1,4-pentadiene, 1,5-hexadiene; 1,6-heptadiene; 1,7-octadiene, 1,8-nonadiene, 1,9-decadiene, 1,11-dodecadiene, 1,13-tetradecadiene, and 1,19-eicosadiene, 1,3-butadiyne, 1,5-hexadiyne (dipropargyl), and 1-hexene-5-yne.

In another embodiment, the component (B) is selected from a $R^6$—$Y^2$—$R^6$ compound where $Y^2$ is a siloxane, herein denoted as ($B^2$). The $Y^2$ siloxane group may be selected from any organopolysiloxane bonded to at least two organic groups having aliphatic unsaturation, designated as $R^6$, to form $R^6$—$Y^2$—$R^6$ structures. Thus, component ($B^2$) can be any organopolysiloxane, and mixtures thereof, comprising at least two siloxane units represented by the average formula $R^5R_mSiO_{(4-m)/2}$
wherein
R is an organic group,
$R^6$ is a monovalent unsaturated aliphatic group as defined above, and
m is zero to 3

The $R^6$ group may be present on any mono, di, or tri siloxy unit in an organopolysiloxane molecule, for example; $(R^6R_2SiO_{0.5})$, $(R^6RSiO)$, or $(R^6SiO_{1.5})$; as well as in combination with other siloxy units not containing an $R^6$ substituent, such as $(R_3SiO_{0.5})$, $(R_2SiO)$, $(RSiO_{1.5})$, or $(SiO_2)$ siloxy units where R is independently any organic group, alternatively a hydrocarbon containing 1 to 30 carbons, alternatively an alkyl group containing 1 to 30 carbons, or alternatively methyl; providing there are at least two $R^6$ substituents in the organopolysiloxane.

Representative, non-limiting, examples of such siloxane based $R^6$—$Y^2$—$R^6$ structures suitable as component ($B^2$) include;

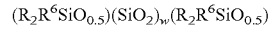

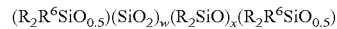

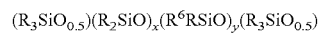

where w≥0, x≥0, y≥2, and z is ≥0, R is an organic group, and
$R^6$ is a monovalent unsaturated aliphatic hydrocarbon group.

$B^2$ may be selected from vinyl functional polydimethylsiloxanes (vinyl siloxanes) or hexenyl functional polydimethylsiloxanes (hexenyl siloxanes), such as those having the average formula;

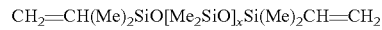

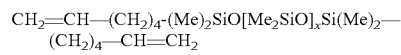

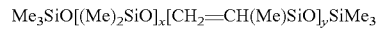

wherein Me is methyl, x≥0, alternatively x is 0 to 200, alternatively x is 10 to 150, y≥2, alternatively y is 2 to 50, alternatively y is 2 to 10.

Vinyl functional polydimethylsiloxanes are known, and there are many commercially available.

Component (C) comprises any catalyst typically employed for hydrosilylation reactions. It is preferred to use platinum group metal-containing catalysts. By platinum group it is meant ruthenium, rhodium, palladium, osmium, iridium and platinum and complexes thereof. Platinum group metal-containing catalysts useful in preparing the compositions of the present invention are the platinum complexes prepared as described by Willing, U.S. Pat. No. 3,419,593, and Brown et al, U.S. Pat. No. 5,175,325, each of which is hereby incorporated by reference to show such complexes and their preparation. Other examples of useful platinum group metal-containing catalysts can be found in Lee et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalysts and methods for their preparation. The platinum-containing catalyst can be platinum metal, platinum metal deposited on a carrier such as silica gel or powdered charcoal, or a compound or complex of a platinum group metal. Preferred platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in U.S. patent application Ser. No. 10/017,229, filed Dec. 7, 2001, such as $(COD)Pt(SiMeCl_2)_2$, where COD is 1,5-cyclooctadiene and Me is methyl. These alkene-platinum-silyl complexes may be prepared, for example by mixing 0.015 mole $(COD)PtCl_2$ with 0.045 mole COD and 0.0612 moles $HMeSiCl_2$.

The appropriate amount of the catalyst will depend upon the particular catalyst used. The platinum catalyst should be present in an amount sufficient to provide at least 2 parts per million (ppm), preferably 4 to 200 ppm of platinum based on total weight percent solids (all non-solvent ingredients) in the composition. It is highly preferred that the platinum is present in an amount sufficient to provide 4 to 150 weight ppm of platinum on the same basis. The catalyst may be added as a single species or as a mixture of two or more different species.

Optional component D) is a compound or mixture of compounds having a mono terminal aliphatic unsaturated hydrocarbon group. Optional component D) may be selected from D') a hydrocarbon containing 6-30 carbons having one terminal unsaturated aliphatic hydrocarbon group, and/or component D") a polyoxyalkylene having one terminal unsaturated aliphatic group.

The addition of component D) can alter the resulting chemical and physical properties of the highly branched organopolysiloxane. For example, selecting D' will result in the addition of hydrocarbon groups to the highly branched organopolysiloxane, thus adding more hydrophobic character to the highly branched organopolysiloxane. Conversely, selecting a polyoxyalkylene having a majority of ethylene oxide units will result in a highly branched organopolysiloxane having increased hydrophilicity.

The unsaturated aliphatic hydrocarbon group in D' or D" can be an alkenyl or alkynyl group. Representative, non-limiting examples of the alkenyl groups are shown by the following structures; $H_2C=CH-$, $H_2C=CHCH_2-$, $H_2C=C(CH_3)CH_2-$, $H_2C=CHCH_2CH_2-$, $H_2C=CHCH_2CH_2CH_2-$, and $H_2C=CHCH_2CH_2CH_2CH_2-$. Representative, non-limiting examples of alkynyl groups are shown by the following structures; $HC\equiv C-$, $HC\equiv CCH_2-$, $HC\equiv CC(CH_3)-$, $HC\equiv CC(CH_3)_2-$, and $HC\equiv CC(CH_3)_2CH_2-$.

Component D'), the hydrocarbon containing 6-30 carbons having one terminal unsaturated aliphatic group, may be selected from alpha olefins such as 1-hexene, 1-octene, 1-decene, 1-undecene, 1-decadecene, and similar homologs. Component D') may also be selected from aryl containing hydrocarbons such as alpha methyl styrene.

Component D") may be selected from those polyoxyalkylenes having the average formula $R^7O-[(C_2H_4O)_{c'}(C_3H_6O)_{d'}(C_4H_8O)_e]-R^8$ where $R^7$ is a monovalent unsaturated aliphatic hydrocarbon group containing 2 to 12 carbon atoms, c' is from 0 to 100, d' is from 0 to 100, e is from 0 to 100, providing the sum of c', d', and e is >0.

$R^8$ is hydrogen, an acyl group, or a monovalent hydrocarbon group containing 1 to 8 carbons. Representative, non-limiting examples of polyoxyalkylenes, useful as component D") include;

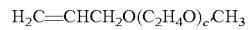

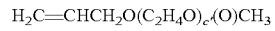

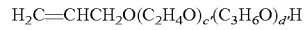

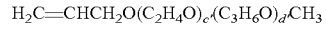

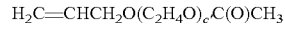

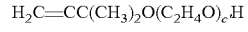

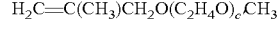

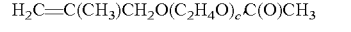

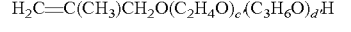

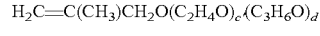

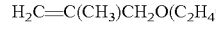

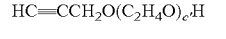

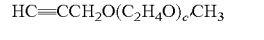

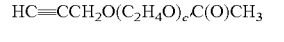

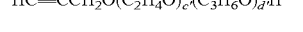

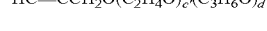

where c' and d' are as defined above.

The polyether may also be selected from those as described in U.S. Pat. No. 6,987,157, which is herein incorporated by reference for its teaching of polyethers.

Components D' or D" may be added to the silicone organic elastomer either during formation (i.e. simultaneously reacting components A), B), C) and D), in a first reaction (for example reacting a partial quantity of SiH groups of component A) with C) and D), followed by further reaction with B) or subsequently added to a formed silicone organic elastomer having SiH content (for example, from unreacted SiH units present on the silicone organic elastomer).

The amount of component D' or D" used in the hydrosilylation reaction may vary, providing the molar quantity of the total aliphatic unsaturated groups present in the reaction from components B) and D) is such that the molar ratio of the SiH units of component A) to the aliphatic unsaturated groups of components B) and D) ranges from 10/1 to 1/10.

In yet another embodiment, a highly branched organopolysiloxane is prepared by reacting;
  a') an organohydrogencyclosiloxane having the formula [(CH$_3$)HSiO]$_g$ where g is 3 to 8, and,
  b') a vinyl terminated polydimethylsiloxane
in the presence of a hydrosilylation catalyst
where the molar ratio of vinyl to SiH in the reaction is between 0.9/1 to 1.2/1.
In this embodiment, an organohydrogencyclosiloxane is reacted with a vinyl terminated polydimethylsiloxane in the presence of a hydrosilylation catalyst.
This reaction is similar to those as described above for preparing highly branched organopolysiloxanes. As such the hydrosilylation catalyst may be any of those as describe above as component C). Similar reaction conditions may be utilized. Typically, the hydrosilylation reaction is conducted in a carrier fluid (as described below).

The organohydrogencyclosiloxanes useful in this embodiment have the formula [(CH$_3$)HSiO]$_g$ where g is 3 to 8, alternatively g is 4 to 6, or alternatively g is 4. The vinyl terminated polydimethylsiloxane may be selected from those having the average formula (CH$_2$=CH)Me$_2$SiO(Me$_2$SiO)$_{dp}$SiMe$_2$(CH=CH$_2$) where dp is the degree of polymerization. In one embodiment, the dp is at least 4000, alternatively, at least 6000, or alternatively at least 9000.

Component b') may be selected from vinyl functional endblocked polydimethylsiloxanes (vinyl siloxanes) or hexenyl functional endblocked polydimethylsiloxanes (hexenyl siloxanes), such as those having the average formula;

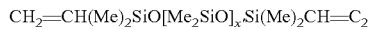

CH$_2$=CH(Me)$_2$SiO[Me$_2$SiO]$_x$Si(Me)$_2$CH=C$_2$

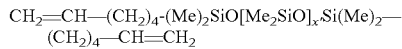

CH$_2$=CH—(CH$_2$)$_4$-(Me)$_2$SiO[Me$_2$SiO]$_x$Si(Me)$_2$—(CH$_2$)$_4$—CH=CH$_2$ wherein Me is methyl,
x'≥50.

Vinyl or hexenyl functional polydimethylsiloxanes are known, and there are many commercially available. Representative, non-limiting examples include DOW CORNING® fluids; SFD 128, DC4-2764, DC2-7891, DC2-7754, DC2-7891, and DC2-7463, SFD-117, SFD-119, SFD 120, SFD 129, DC 5-8709, LV, 2-7038, DC 2-7892, 2-7287, 2-7463, and dihexenyl terminal DC7692, DC7697 (Dow Corning Corporation, Midland, Mich.).

In one embodiment, the vinyl terminated polydimethylsiloxane is selected from a polydimethylsiloxane gum. As used herein, polydimethylsiloxane gums are organopolysiloxanes comprising predominately D siloxy units and are of sufficient molecular weight to impart pituitous behavior to the silicone fluid compositions. Alternatively, the polydimethylsiloxane gum is of sufficient molecular weight to impart a viscosity of at least 1,000,000 mm$^2$/s at 25° C., or alternatively 2,000,000 mm$^2$/s at 25° C. Alternatively, the molecular weight of the polydimethylsiloxane gum is sufficient to impart a Williams plasticity number of at least 40 as determined by the American Society for Testing and Materials (ASTM) test method 926. Typically, the plasticity number should be 40 to 200, or alternatively 50 to 150. Alternatively, the molecular weight of the polydimethylsiloxane gum is at least 600,000 Daltons, or alternatively at least 1,000,000 Daltons, or alternatively at least 2,000,000 Daltons.

Methods for preparing polydimethylsiloxane gums are well known and many are commercially available. Representative commercial products suitable in the present silicone compositions include; Dow Corning® SGM-36 Gum and SGM-3 Gum.

The amounts of a') the organohydrogencyclosiloxane and b') the vinyl terminated polydimethylsiloxane may vary, but typically are such so as to provide a molar ratio of vinyl to SiH to be 0.9/1 to 1.2/1, or alternatively from 0.95/1 to 1.1/1. The total amounts of a' and b' used are such so as to provide a solids content of at least 5 wt %, alternatively at least 10 wt %, or alternatively at least 20 wt %.

Carrier Fluid

The organopolysiloxanes as described above may be dispersed in an optional carrier fluid. Suitable carrier fluids include silicones, both linear and cyclic, organic oils, organic solvents and mixtures of these. Specific examples of solvents may be found in U.S. Pat. No. 6,200,581, which is hereby incorporated by reference for this purpose.

Typically, the carrier fluid is a low viscosity silicone or a volatile methyl siloxane or a volatile ethyl siloxane or a volatile methyl ethyl siloxane having a viscosity at 25° C. in the range of 1 to 1,000 mm$^2$/sec such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, hexamethyl-3,3,bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes.

Organic solvents may be exemplified by, but not limited to, aromatic hydrocarbons, aliphatic hydrocarbons, alcohols, aldehydes, ketones, amines, esters, ethers, glycols, glycol ethers, alkyl halides and aromatic halides. Hydrocarbons including isododecane, isohexadecane, Isopar L (C11-C13), Isopar H(C11-C12), hydrogentated polydecene. Ethers and esters including isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic carrier fluids suitable as a stand alone compound or as an ingredient to the carrier fluid include fats, oils, fatty acids, and fatty alcohols.

The amount of carrier fluid is such that there is 0 to 98 weight percent, alternatively 0.5 to 90 weight percent, alternatively 5 to 80 weight percent, of carrier fluid in the silicone fluid composition containing organopolysiloxane.

The silicone pituitous fluid compositions as discussed above may be provided as an emulsion. As used herein, "emulsion" is meant to encompass water continuous emulsions (for example an oil in water type emulsion, or a silicone in water emulsion), oil or silicone continuous emulsions (water in oil emulsions or water in silicone emulsions), or multiple emulsions (water/oil/water, oil/water/oil types, water/silicone/water, or silicone/water/silicone). The silicone pituitous fluid compositions formed may be added to any type of emulsion by common mixing techniques. There are no special requirements or conditions needed to effect the mixing of silicone pituitous fluid compositions to form an emulsion. Mixing techniques can be simple stirring, homogenizing, sonalating, and other mixing techniques known in the art to effect the formation of vesicles in aqueous dispersions. The mixing can be conducted in a batch, semi-continuous, or continuous process.

The amount of the silicone pituitous fluid composition added to form the emulsion can vary and is not limited, however the amounts typically may range from a vesicle/emulsion weight ratio of 0.1/99 to 99/0.1, alternatively 1/99 to 99/1.

The emulsions used may be w/o, w/s, or multiple phase emulsions using silicone emulsifiers. Typically the water-in-silicone emulsifier in such formulation is non-ionic and is selected from polyoxyalkylene-substituted silicones, silicone alkanolamides, silicone esters and silicone glycosides. Silicone-based surfactants may be used to form such emulsions and are well known in the art, and have been described for example in U.S. Pat. No. 4,122,029 (Gee et al.), U.S. Pat. No. 5,387,417 (Rentsch), and U.S. Pat. No. 5,811,487 (Schulz et al).

When the emulsion is an oil-in-water emulsion, it may include common ingredients generally used for preparing emulsions such as but not limited to non ionic surfactants well known in the art to prepare o/w emulsions. Examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants.

Personal Care Product Compositions

The pituitous silicone fluids compositions, or emulsions thereof, may be formulated into personal care products. The personal care compositions of this disclosure may be in the form of a cream, a gel, a powder, a paste, or a freely pourable liquid. Generally, such compositions can generally be prepared at room temperature if no solid materials at room temperature are presents in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care products may be functional with respect to the portion of the body to which they are applied, cosmetic, therapeutic, or some combination thereof. Conventional examples of such products include, but are not limited to: antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including antiacne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

The present compositions can be used in a variety of personal, household, and healthcare applications. In particular, the compositions of the present invention may be used in the personal care products as taught in U.S. Pat. Nos. 6,051,216, 5,919,441, 5,981,680; as disclosed in WO 2004/060271 and WO 2004/060101; in sunscreen compositions as taught in WO 2004/060276; in cosmetic compositions also containing film-forming resins, as disclosed in WO 03/105801; in the cosmetic compositions as taught in US Patent Application Publications 2003/0235553, 2003/0072730, 2003/0170188, EP 1,266,647, EP 1,266,648, EP1,266,653, WO 03/105789, WO 2004/000247 and WO 03/106614; as additional agents to those taught in WO 2004/054523; in long wearing cosmetic compositions as taught in US Patent Application Publication 2004/0180032; in transparent or translucent care and/or make up compositions as discussed in WO 2004/054524; all of which are incorporated herein by reference.

The compositions according to this invention can be used by the standard methods, such as applying them to the human body, e.g. skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the compositions according to the present invention may be used in a conventional manner for example for conditioning the skin. An effective amount of the composition for the purpose is applied to the skin. Such effective amounts generally range from 1 mg/cm$^2$ to 3 mg/cm$^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the compositions according to the invention on hair may use a conventional manner for conditioning hair. An effective amount of the composition for conditioning hair is applied to the hair. Such effective amounts generally range from 1 g to 50 g, preferably from 1 g to 20 g. Application to the hair typically includes working the composition through the hair such that most or all of the hair is contacted with the composition. This method for conditioning the hair comprises the steps of applying an effective amount of the hair care composition to the hair, and then working the composition through the hair. These steps can be repeated as many times as desired to achieve the desired conditioning benefit.

Non-limiting examples of additives which may be formulated into the personal care compositions in addition to the pituitous silicone fluids include: additional silicones, antioxidants, cleansing agents, colorants, additional conditioning agents, deposition agents, electrolytes, emollients and oils, exfoliating agents, foam boosters, fragrances, humectants, occlusive agents, pediculicides, pH control agents, pigments, preservatives, biocides, other solvents, stabilizers, sunscreening agents, suspending agents, tanning agents, other surfactants, thickeners, vitamins, botanicals, waxes, rheology-modifying agents, anti-dandruff, anti-acne, anti-carie and wound healing-promotion agents.

The personal care composition, such as a shampoo or cleanser may contain at least one anionic detersive surfactant. This can be any of the well-known anionic detersive surfactants typically used in shampoo formulations. These anionic detersive surfactants function as cleansing agents and foaming agents in the shampoo compositions of this invention. The anionic detersive surfactants are exemplified by alkali metal sulforicinates, sulfonated glyceryl esters of fatty acids such as sulfonated monoglycerides of coconut oil acids, salts of sulfonated monovalent alcohol esters such as sodium oleyl-isethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid. Preferably the detersive surfactant is selected from the group consisting of sodium lauryl sulfate, ammonium lauryl sulfate, triethanolamine lauryl sulfate, sodium lauryl ether sulfate, and ammonium lauryl ether sulfate. The anionic detersive surfactant is present in the shampoo compositions of this invention in an amount from 5 to 50 wt % and preferably 5 to 25 wt % based on the total weight of the composition.

The personal care composition may contain at least one cationic deposition aid, preferably a cationic deposition polymer. The cationic deposition aid will generally be present at levels of from 0.001 to 5%, preferably from 0.01 to 1%, more preferably from 0.02% to 0.5% by weight. The polymer may be a homopolymer or be formed from two or more types of monomers. The molecular weight of the polymer will generally be between 5,000 and 10,000,000, typically at least 10,000 and preferably in the range 100,000 to 2,000,000. The polymers will have cationic nitrogen containing groups such as quaternary ammonium or protonated amino groups, or a mixture thereof. The cationic charge density has been found to need to be at least 0.1 meq/g, preferably above 0.8 or higher. The cationic charge density should not exceed 4 meq/g, it is preferably less than 3 and more preferably less than 2 meq/g. The charge density can be measured using the Kjeldahl method and should be within the above limits at the desired pH of use, which will in general be from 3 to 9 and preferably between 4 and 8. The cationic nitrogen-containing group will generally be present as a substituent on a fraction of the total monomer units of the cationic deposition polymer. Thus when the polymer is not a homopolymer it can contain spacer noncationic monomer units. Such polymers are described in the CTFA Cosmetic Ingredient Directory, 3rd edition. Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyil substituted monomers preferably have C1-C7 alkyl groups, more preferably C1-3 alkyl groups. Other suitable spacers include vinyl esters, vinyl alcohol, maleic anhydride, propylene glycol and ethylene glycol. The cationic amines can be primary, secondary or tertiary amines, depending upon the particular species and the pH of the composition. In general secondary and tertiary amines, especially tertiary, are preferred. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$-$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydrocarbyls, more preferably $C_1$-$C_3$ alkyls. The cationic deposition aids can comprise mixtures of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g., Chloride salt) (referred to in the industry by the Cosmetic, Toiletry, and Fragrance Association, "CTFA". as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g., GAFQUAT 755N); cationic diallyl quaternary ammonium-containing polymer including, for example, dimethyl diallyammonium chloride homopolymer and copolymers of acrylamide and dimethyl diallyammonium chloride, referred to in the industry (CTFA) as Polyquaternium 6 and Polyquaternium 7, respectively; mineral acid salts of aminoalkyl esters of homo- and co-polymers of unsaturated carboxylic acids having from 3 to 5 carbon atoms, as described in U.S. Pat. No. 4,009,256; and cationic polyacrylamides as described in our copending UK Application No. 9403156.4 (WO95/22311). Other cationic deposition aids that can be used include polysaccharide polymers, such as cationic cellulose derivatives and cationic starch derivatives. Cationic polysaccharide polymer materials suitable for use in compositions of the invention include those of the formula: $A-O(R-N^+R^1R^2R^3X^-)$ wherein: A is an anhydroglucose residual group, such as starch or cellulose anhydroglucose residual, R is an alkylene oxyalklene, polyoxyalkylene, or hydroxyalkylene group, or combination thereof, $R^1$, $R^2$ and $R^3$ independently are alkyl, aryl, alkylaryl, arylalkyl, alkoxyalkyl, or alkoxyaryl groups, each group containing up to 18 carbon atoms, and the total number of carbon atoms for each cationic moiety (i.e., the sum of carbon atoms in $R^1$, $R^2$, $R^3$) preferably being 20 or less, and X is an anionic counterion, as previously described. Cationic cellulose is available from Amerchol Corp. (Edison, N.J., USA) in their Polymer iR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

The personal care composition may contain a foam boosting agent. A foam booster is an agent which increases the amount of foam available from a system at a constant molar concentration of surfactant, in contrast to a foam stabilizer which delays the collapse of a foam. Foam building is provided by adding to the aqueous media, a foam boosting effective amount of a foam boosting. The foam boosting agent is preferably selected from the group consisting of fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) C12-15 alkoxypropylamine oxide. Preferably a foam booster is selected from the group consisting of lauric acid diethanolamide, N-lauryl dimethylamine oxide, coconut acid diethanolamide, myristic acid diethanolamide, and oleic acid diethanolamide. The foam boosting agent is preferably present in the shampoo compositions of this invention in an amount from 1 to 15 wt % and more preferably 2 to 10 wt % based on the total weight of the composition. The composition may further comprise a polyalkylene glycol to improve lather performance. Concentration of the polyalkylene glycol in the shampoo composition may range from 0.01% to 5%, preferably from 0.05% to 3%, and more preferably from 0.1% to 2%, by weight of the composition. The optional polyalkylene glycols are characterized by the general formula: H(OCH2CHR)n-OH wherein R is selected from the group consisting of H, methyl, and mixtures thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist. In the above structure, n has an average value of from 1500 to 25,000, preferably from 2500 to 20,000, and more preferably from 3500 to 15,000. Polyethylene glycol polymers useful herein are PEG-2M wherein R equals H and n has an average value of 2,000 (PEG-2M is also known as Polyox WSR9N-10, which is available from Union Carbide and as PEG-2,000); PEG-5M wherein R equals H and n has an average value of 5,000 (PEG-5M is also known as Polyox WSRO N-35 and Polyox WSRS N-80, both available from Union Carbide and as PEG-5,000 and Polyethylene Glycol 300,000); PEG-7M wherein R equals H and n has an average value of 7,000 (PEG-7M is also known as Polyox WSRO N-750 available from Union Carbide); PEG-9M wherein R equals H and n has an average value of 9,000 (PEG 9-M is also known as Polyox WSRS N-3333 available from Union Carbide); and PEG-14 M wherein R equals H and n has an average value of 14,000 (PEG-14M is also known as Polyox WSRO N-3000 available from Union Carbide). Other useful polymers include the polypropylene glycols and mixed polyethylene/polypropylene glycols.

The personal care composition may contain a suspending agent at concentrations effective for suspending the preferred silicone conditioning agent, or other water-insoluble material, in dispersed form in the shampoo compositions. Such concentrations range from 0.1% to 10%, preferably from 0.3% to 5.0%, by weight of the shampoo compositions. Suspending agents include crystalline suspending agents which can be categorized as acyl derivatives, long chain amine oxides, and mixtures thereof, concentrations of which range from 0.1% to 5.0%, preferably from 0.5% to 3.0%, by weight of the shampoo compositions. These suspending agents are described in U.S. Pat. No. 4,741,855, which description is incorporated herein by reference. These preferred suspending agents include ethylene glycol esters of fatty acids preferably having from 16 to 22 carbon atoms. More preferred are the ethylene glycol stearates, both mono and distearate, but particularly the distearate containing less than 7% of the mono stearate. Other suitable suspending agents include alkanol amides of fatty acids, preferably having from 16 to 22 carbon atoms, more preferably 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having C8-C22 chains may be used. Other long chain acyl derivatives suitable for use as suspending agents include N,N-dihydrocarbyl amido benzoic acid and soluble salts thereof (e.g., Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl (C16-C22) dimethyl amine oxides, e.g., stearyl dimethyl amine oxide. Other suitable suspending agents include xanthan gum at concentrations ranging from 0.3% to 3%, preferably from 0.4% to 1.2%, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions. Such combinations are described in U.S. Pat. No. 4,704,272, which description is incorporated herein by reference. Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956, available from B.F. Goodrich Company. Other suitable suspending agents include primary amines having a fatty alkyl moiety having at least 16 carbon atoms, examples of which include palmitamine or stearamine, and secondary amines having two fatty alkyl moieties each having at least 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer. Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc.

The personal care composition may contain one or more water-soluble emollients including, but not limited to, lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by one skilled in the art.

The personal care composition may contain various oils. The term "oil" as used herein refers to any material which is substantially insoluble in water. When the composition is to be used in a cosmetic or personal care product, the product components must also be cosmetically acceptable or otherwise meet the conditions of the end use product. Suitable oil components include, but are not limited to, natural oils such as coconut oil; hydrocarbons such as mineral oil and hydrogenated polyisobutene; fatty alcohols such as octyldodecanol; esters such as C12-C15 alkyl benzoate; diesters such as propylene dipelarganate; and triesters, such as glyceryl trioctanoate and silicones especially cyclomethicone and dimethicone and mixtures thereof. The composition of the invention also contains oils, preferably a mixture of low viscosity and high viscosity oils. Suitable low viscosity oils have a viscosity of 5 to 100 mPa·s at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, cocodicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof. The high viscosity surface oils generally have a viscosity of 200-1,000,000 mPa·s at 25° C., preferably a viscosity of 100,000-250,000 mPa·s. Surface oils include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof. The suggested ratio of low viscosity to high viscosity oils in the oil phase is 1:15 to 15:1, preferably 1:10 to 10:1 respectively. The preferred formulation of the invention comprises 1 to 20% of a mixture of low viscosity and high viscosity surface oils.

Mention may be made, among the optional other non-silicone fatty substances, of mineral oils, such as liquid paraffin or liquid petroleum, of animal oils, such as perhydrosqualene or arara oil, or alternatively of vegetable oils, such as sweet almond, calophyllum, palm, castor, avocado, jojaba, olive or cereal germ oil. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The personal care composition may contain various waxes. The waxes or wax-like materials generally have a melting point range of 35 to 120° C. at atmospheric pressure. Waxes in this category include synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or mixtures thereof. The preferred formulation of the invention comprises 10-30% of a mixture of waxes. Mention may be made, among the waxes capable of begin used as non-silicone fatty substances, of animal waxes, such as beeswax; vegetable waxes, such as carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

The personal care composition may contain various powders. The powder component of the invention can be generally defined as dry, particulate matter having a particle size of 0.02-50 microns. The particulate matter may be colored or non-colored (for example white). Suitable powders include bismuth oxychloride, titanated mica, fumed silica, spherical silica beads, polymethylmethacrylate beads, micronized teflon, boron nitride, acrylate polymers, aluminum silicate, aluminum starch octenylsuccinate, bentonite, calcium silicate, cellulose, chalk, corn starch, distomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, serecite, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature.

The powder component also comprises various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides.

A pulverulent colouring agent, such as carbon black, chromium or iron oxides, ultramarines, manganese pyrophosphate, iron blue, and titanium dioxide, pearlescent agents, generally used as a mixture with coloured pigments, or some organic dyes, generally used as a mixture with coloured pigments and commonly used in the cosmetics industry, can be added to the composition. In general, these colouring agents can be present in an amount by weight from 0 to 20% with respect to the weight of the final composition.

Pulverulent inorganic or organic fillers can also be added, generally in an amount by weight from 0 to 40% with respect to the weight of the final composition. These pulverulent fillers can be chosen from talc, micas, kaolin, zinc or titanium oxides, calcium or magnesium carbonates, silica, spherical titanium dioxide, glass or ceramic beads, metal soaps derived from carboxylic acids having 8-22 carbon atoms, non-expanded synthetic polymer powders, expanded powders and powders from natural organic compounds, such as cereal starches, which may or may not be crosslinked. The fillers may preferably be present in a proportion of from 0 to 35% of the total weight of the composition, more preferably 5 to 15%. Mention may be made in particular of talc, mica, silica, kaolin, nylon powders (in particular ORGASOL), polyethylene powders, Teflon, starch, boron nitride, copolymer microspheres such as EXPANCEL (Nobel Industrie), polytrap and silicone resin microbeads (TOSPEARL from Toshiba, for example).

The personal care composition may contain sunscreens. These include those which absorb ultraviolet light between 290-320 nanometers (the UV-B region) such as, but not exclusively, para-aminobenzoic acid derivatives and cinnamates such as octyl methoxycinnamate and those which absorb ultraviolet light in the range of 320-400 nanometers (the UV-A region) such as benzophenones and butyl methoxy dibenzoylmethane. Some additional examples of sunscreen chemicals which may be employed in accordance with the present invention are 2-ethoxyethyl p-methoxycinnamate; menthyl anthranilate; homomethyl salicylate; glyceryl p-aminobenzoate; isobutyl p-aminobenzoate; isoamyl p-dimethylaminobenzoate; 2-hydroxy-4-methoxybenzophenones sulfonic acid; 2,2'-dihydroxy-4-methoxybenzophenone; 2-hydroxy-4-methoxybenzophenone; 4-mono and 4-bis(3-hydroxy-propyl)amino isomers of ethyl benzoate; and 2-ethylhexyl p-dimethylaminobenzoate. As hydrophilic screening agents which can be used in the invention, mention may be made of those described in Application EP-A-678, 292. These hydrophilic screening agents are those containing at least one carboxylic or better still sulphonic acid radical. This acid radical can be in free form or in partially or totally neutralized form. It is possible to use one or more hydrophilic screening agents containing acid functionality. As examples of acidic screening agents containing at least one $SO_3H$ group, mention may be made more particularly of 3-benzylidine-2-camphorsulphonic derivatives. A particularly preferred compound is benzene-1,4-[di(3-methylidenecamphor-10-sulphonic acid)]. This screening agent is a broad-band screening agent capable of absorbing ultraviolet rays with wavelengths of between 280 nm and 400 nm, with absorption maxima of between 320 nm and 400 nm, in particular at 345 nm. It is used in acid form or salified with a base chosen from triethanolamine, sodium hydroxide and potassium hydroxide. In addition, it can be in cis or trans form. This screening agent is known under the trade name Mexoryl SX. Other specific examples are 4-(3-methylidenecamphor)benzenesulphonic acid, 3-benzylidenecamphor-10-sulphonic acid, 2-methyl-5-(3-methylidenecamphor)benzenesulphonic acid, 2-chloro-5-(3-methylidenecamphor)benzenesulphonic acid, 3-(4-methyl)benzylidenecamphor-10-sulphonic acid, (3-t-butyl-2-hydroxy-5-methyl)benzylidenecamphor-10-sulphonic acid, (3-t-butyl-2-hydroxy-5-methoxy)benzylidenecamphor-10-sulphonic acid, (3,5-di-tert-butyl-4-hydroxy)benzylidenecamphor-10-sulphonic acid, 2-methoxy-5-(3-methylidenecamphor)benzenesulphonic acid, 3-(4,5-methylenedioxy)benzylidenecamphor-10-sulphonic acid, 3-(4-methoxy)benzylidenecamphor-10-sulphonic acid, 3-(4,5-dimethoxy)benzylidenecamphor-10-sulphonic acid, 3-(4-n-butoxy)benzylidenecamphor-10-sulphonic acid, 3-(4-n-butoxy-5-methoxy)benzylidenecamphor-10-sulphonic acid, 2-[4-(camphormethylidene)phenyl]benzimidazole-5-sulphonic acid. Suitable compounds are described in U.S. Pat. No. 4,585,597, patent applications FR 2,236,515, 2,282,426, 2,645,148, 2,430,938 and 2,592,380. The screening agent containing a sulphonic group can also be a sulphonic derivative of benzophenone or 2-phenylbenzimidazole-5-sulphonic acid, having excellent photoprotective power in the UV-B radiation range and is sold under the trade name "Eusolex 232" by the company Merck, benzene-1,4-di(benzimidazol-2-yl-5-sulphonic acid), benzene-1,4-di(benzoxazol-2-yl-5-sulphonic acid). The hydrophilic screening agent(s) can be present in the final composition according to the invention in a content which can range from 0.1 to 20%, preferably from 0.2 to 10%, by weight relative to the total weight of the composition.

As lipophilic screening agents which can be used in the invention, mention may be made advantageously of the family of screening agents derived from dibenzoylmethane and more especially 4-tert-butyl-4'-methoxydibenzoylmethane, which effectively have a high intrinsic power of absorption. These dibenzoylmethane derivatives, which are products that are well known per se as UV-A active screening agents, are described in particular in French patent applications FR-A-2,326,405 and FR-A-2,440,933, as well as in European patent application EP-A-0,114,607; 4-(tert-butyl)-4'-methoxydibenzoylmethane is moreover currently sold under the trade name "Parsol 1789" by the company Givaudan. Another dibenzoylmethane derivative which is preferred according to the present invention is 4-isopropyldibenzoylmethane, this screening agent being sold under the name "Eusolex 8020" by the company Merck. Similarly octocrylene, a liquid lipophilic screening agent that is already known for its activity in the UV-B range is commercially available, and is sold in particular under the name "Uvinul N 539" by the company BASF. As another lipophilic (or liposoluble) screening agent which can be used in the invention, mention may also be made of p-methylbenzylidenecamphor, which is also known as a UV-B absorber and is sold in particular under the trade name "Eusolex 6300" by the company Merck. The lipophilic screening agent(s) can be present in the composition according to the invention in a content which can range from 0.5 to 30%, preferably from 0.5 to 20%, of the total weight of the composition. Other examples of lipophilic or hydrophilic organic screening agents are given in particular in patent application EP-A-0,487,404. The cosmetic and/or dermatological compositions according to the invention can also contain pigments or alternatively nanopigments (average primary particle size: generally between 5 nm and 100 nm, preferably between 10 and 50 nm) of coated or uncoated metal oxides, such as, for example, nanopigments of titanium oxide (amorphous or crystallized in rutile and/or anatase form), of iron oxide, of zinc oxide, of zirconium oxide or of cerium oxide, which are all photoprotective agents that are well known per se and which act by physically blocking (reflection and/or scattering) UV radiation. Standard coating agents are, moreover, alumina and/or aluminium stearate, and silicones. Such coated or uncoated metal oxide nanopigments are described in particular in patent applications EP-A-0,518,772 and EP-A-0,518,773.

Thickening agent may be added to provide a convenient viscosity. For example, viscosities within the range of 500 to 25,000 mm$^2$/s at 25° C. or more alternatively in the range of 3,000 to 7,000 mm$^2$/s are usually suitable. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by methylcellulose, methylhydroxypropylcellulose, hydroxypropylcellulose, polypropylhydroxyethylcellulose, starch, and starch derivatives exemplified by hydroxyethylamylose and starch amylose, locust bean gum, electrolytes exemplified by sodium chloride and ammonium chloride, and saccharides such as fructose and glucose, and derivatives of saccharides such as PEG-120 methyl glucose diolate or mixtures of 2 or more of these. Alternatively the thickening agent is selected from cellulose derivatives, saccharide derivatives, and electrolytes, or from a combination of two or more of the above thickening agents exemplified by a combination of a cellulose derivative and any electrolyte, and a starch derivative and any electrolyte. The thickening agent, where used is present in the shampoo compositions of this invention in an amount sufficient to provide a viscosity in the final shampoo composition of from 500 to 25,000 mm$^2$/s. Alternatively the thickening agent is present in an amount from 0.05 to 10 wt % and alternatively 0.05 to 5 wt % based on the total weight of the composition.

Stabilizing agents can be used in the water phase of the compositions. Suitable water phase stabilizing agents can include alone or in combination one or more electrolytes, polyols, alcohols such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to 0.1 to 5 wt % and more alternatively 0.5 to 3 wt % of the total composition. The hydrocolloids include gums, such as Xantham gum or Veegum and thickening agents, such as carboxymethyl cellulose. Polyols, such as glycerine, glycols, and sorbitols can also be used. Alternative polyols are glycerine, propylene glycol, sorbitol and butylene glycol. If a large amount of a polyol is used, one need not add the electrolyte. However, it is typical to use a combination of an electrolyte, a polyol and an hydrocolloid to stabilize the water phase, e.g. magnesium sulfate, butylene glycol and Xantham gum.

The silicone emulsions can also be used in anti-perspirant and deodorant compositions under but not limited to the form of sticks, soft solid, roll on, aerosol, and pumpsprays. Some examples of antiperspirant agents and deodorant agents are Aluminum Chloride, Aluminum Zirconium Tetrachlorohydrex GLY, Aluminum Zirconium Tetrachlorohydrex PEG, Aluminum Chlorohydrex, Aluminum Zirconium Tetrachlorohydrex PG, Aluminum Chlorohydrex PEG, Aluminum Zirconium Trichlorohydrate, Aluminum Chlorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG, Chlorophyllin-Copper Complex, Triclosan, Aluminum Zirconium Octachlorohydrate, and Zinc Ricinoleate.

The composition according to the invention can also be under the form of aerosols in combination with propellant gases, such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

Silicone compositions other than the present pituitous silicone fluid compositions, may also be included in the personal care compositions. For example, such silicones include; silicone fluids, gums, resins, elastomers; silicone surfactants and emulsifiers such as silicone polyethers, organofunctional silicones such as aminofunctional silicones and alkylmethylsiloxanes.

Alkylmethylsiloxanes may be included in the present compositions. These siloxane polymers generally will have the formula Me$_3$SiO[Me$_2$SiO]$_y$[MeRSiO]$_z$SiMe$_3$, in which R is a hydrocarbon group containing 6-30 carbon atoms, Me represents methyl, and the degree of polymerization (DP), i.e., the sum of y and z is 3-50. Both the volatile and liquid species of alkymethysiloxanes can be used in the composition.

Silicone gums may be included in the present compositions. Polydiorganosiloxane gums are known in the art and are available commercially. They consist of generally insoluble polydiorganosiloxanes having a viscosity in excess of 1,000,000 centistoke (mm$^2$/s) at 25° C., alternatively greater than 5,000,000 centistoke (mm$^2$/s) at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity greater than 5 million centistoke (mm$^2$/s) at 25° C., to 20 million centistoke (mm$^2$/s) at 25° C. Compositions of this type in the form of suspensions are most preferred, and are described for example in U.S. Pat. No. 6,013,682 (Jan. 11, 2000).

Silicone resins may be included in the present compositions. These resin compositions are generally highly crosslinked polymeric siloxanes. Crosslinking is obtained by incorporating trifunctional and/or tetrafunctional silanes with the monofunctional silane and/or difunctional silane monomers used during manufacture. The degree of crosslinking required to obtain a suitable silicone resin will vary according to the specifics of the silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be considered to be suitable for use as the silicone resin. Commercially available silicone resins suitable for applications herein are generally supplied in an unhardened form in low viscosity volatile or nonvolatile silicone fluids. The silicone resins should be incorporated into compositions of the invention in their non-hardened forms rather than as hardened resinous structures.

Silicone carbinol Fluids may be included in the present compositions. These materials are described in WO 03/101412 A2, and can be commonly described as substituted hydrocarbyl functional siloxane fluids or resins.

Water soluble or water dispersible silicone polyether compositions may be included in the present compositions: These are also known as polyalkylene oxide silicone copolymers, silicone poly(oxyalkylene) copolymers, silicone glycol copolymers, or silicone surfactants. These can be linear rake or graft type materials, or ABA type where the B is the siloxane polymer block, and the A is the poly(oxyalkylene) group. The poly(oxyalkylene) group can consist of polyethylene oxide, polypropylene oxide, or mixed polyethylene oxide/polypropylene oxide groups. Other oxides, such as butylene oxide or phenylene oxide are also possible.

Compositions according to the invention can be used in w/o, w/s, or multiple phase emulsions using silicone emulsifiers. Typically the water-in-silicone emulsifier in such formulation is non-ionic and is selected from polyoxyalkylene-substituted silicones, silicone alkanolamides, silicone esters and silicone glycosides. Suitable silicone-based surfactants are well known in the art, and have been described for example in U.S. Pat. No. 4,122,029 (Gee et al.), U.S. Pat. No. 5,387,417 (Rentsch), and U.S. Pat. No. 5,811,487 (Schulz et al).

EXAMPLES

These examples are intended to illustrate the invention to one of ordinary skill in the art and should not be interpreted as limiting the scope of the invention set forth in the claims. All measurements and experiments were conducted at 23° C., unless indicated otherwise.

The rheological properties of the silicone fluid compositions of these Examples were assessed with a controlled-stress rheometer (TA Instruments AR 1000-N (109 Lukens Drive, New Castle Del. 19720)). Normal force under shear was measured by placing the silicone fluid between a flat disk (attached to the rheometer) and a stationary plate equipped with a load cell. A controlled amount of force (torque) was applied to the shaft attached to the disc thus subjecting the sample to a shear stress. For these experiments, the torque was increased during the experiment and the disc rotated at an increasing rate which was recorded as the shear rate. As the fluid sample was subjected to the shear stress, the normal force was recorded by the load cell.

Example 1

The following silicone fluid compositions were evaluated in this Example.
Sample 1A is Dow Corning® 200 Fluid/1000 cSt (linear polydimethylsiloxane)
Sample 1B is SGM-36 diluted to 15% with Dow Corning® 200 Fluid/5 cSt
Sample 1C is SGM-36 diluted to 18% with Dow Corning® 200 Fluid/5 cSt
Sample 1D is SGM-36 diluted to 20% with Dow Corning® 200 Fluid/5 cSt
Sample 1E is SGM-36 diluted to 35% with a 50:50 wt:wt mixture of Isopar L (a mixture of C11-13 isoparaffins supplied by Exxon) and Isohexadecane (supplied by Ineos).
SGM-36=a silanol-terminated gum sold by Dow Corning Corp. as DOW CORNING SGM-36
The dilutions of SGM-36 in were made my dispersing the gum into the indicated solvent
Sample 1F is an Ultra High M.W. Gum diluted to 15% with Dow Corning® 200 Fluid/5 cSt
Sample 1G is an Ultra High M.W. Gum diluted to 20% with Dow Corning® 200 Fluid/5 cSt
Ultra High M.W. Gum=a silicone gum prepared as follows: a solution of 1000 grams silanol ended polydimethylsiloxane fluid (Mw 2500, dp 34) and 1000 grams xylene as a non-reactive diluent were blended in a sigma blade mixer equipped with $N_2$ purge and vacuum. The mixture was heated to 80° C. and was then catalyzed with 0.6 grams of a phosphonitrosyl chloride catalyst solution (5%). The system was mixed and evacuated to remove water of condensation via azeotropic distillation. Separated xylene solvent was returned to the reactor from the condenser. The reaction proceeded until a solution viscosity of 2,990,000 cSt was reached. The catalyst was neutralized by the addition of THA (trihexylamine). This yielded a polymer in xylene. Dow Corning® 200 Fluid/5 cSt was used to dilute the gum solution in xylene to 15% and 20% polymer.

FIG. 1 displays a plot of the Normal Stress (Pa) vs Shear Rate (1/sec) for each silicone fluid composition measured in this Example using the controlled stress rheometer, as detailed above. In FIG. 1 (and subsequent figures) the line labeled "LIMIT" indicates the boundary considered to be pituitous for the purpose of this disclosure. The LIMIT line was created using the equation y=3.6x, where y in the normal force and x is the shear rate. So to be considered a pituitous fluid for the purpose of this disclosure, the plot of normal force versus shear rate must fall above the LIMIT line.

Example 2

The pituitous behavior of several branched siloxane fluids with vinyl functionality (vinyl branched siloxanes, or VBS) were evaluated in this Example. The VBS fluids evaluated were prepared by equilibration of tetrakis(vinyldimethylsiloxy)silane with dimethyl cyclic siloxanes, as detailed below.

VBS polymers were prepared via a two-step process, as taught in U.S. Pat. No. 6,806,339. First, tetrakis(vinyldimethylsiloxy)silane was prepared by reacting 208.33 grams (1 mol) of tetraethoxyorthosilicone (TEOS) with 186.4 grams (1 mol) of divinyltetramethyldisiloxane using 0.08 grams (0.0005 mols) trifluoromethane sulfonic acid as the catalyst and 36.93 grams (2.05 mols) of water.

VBS-1 was made by equilibrating tetrakis(vinyldimethylsiloxy)silane with dimethyl cyclic siloxanes using a strong basic catalyst (trimethyl amine hydroxide phosphazene). For VBS-1, the ratio of tetrakis(vinyldimethylsiloxy)silane to dimethyl cyclic siloxane was approximately 1:99. The dilutions (80% and 60% VBS-1) were prepared my mixing VBS-1 with Dow Corning® 200 Fluid/5 cSt. VBS-2 is a higher molecular weight material that was prepared in a similar manner as to VBS-1 except that the ratio of tetrakis(vinyldimethylsiloxy)silane to dimethyl cyclic siloxane was approximately 266:1. The dilution (40% VBS-2) was prepared my mixing VBS-2 with Dow Corning® 200 Fluid/5 cSt.

Figure 2:
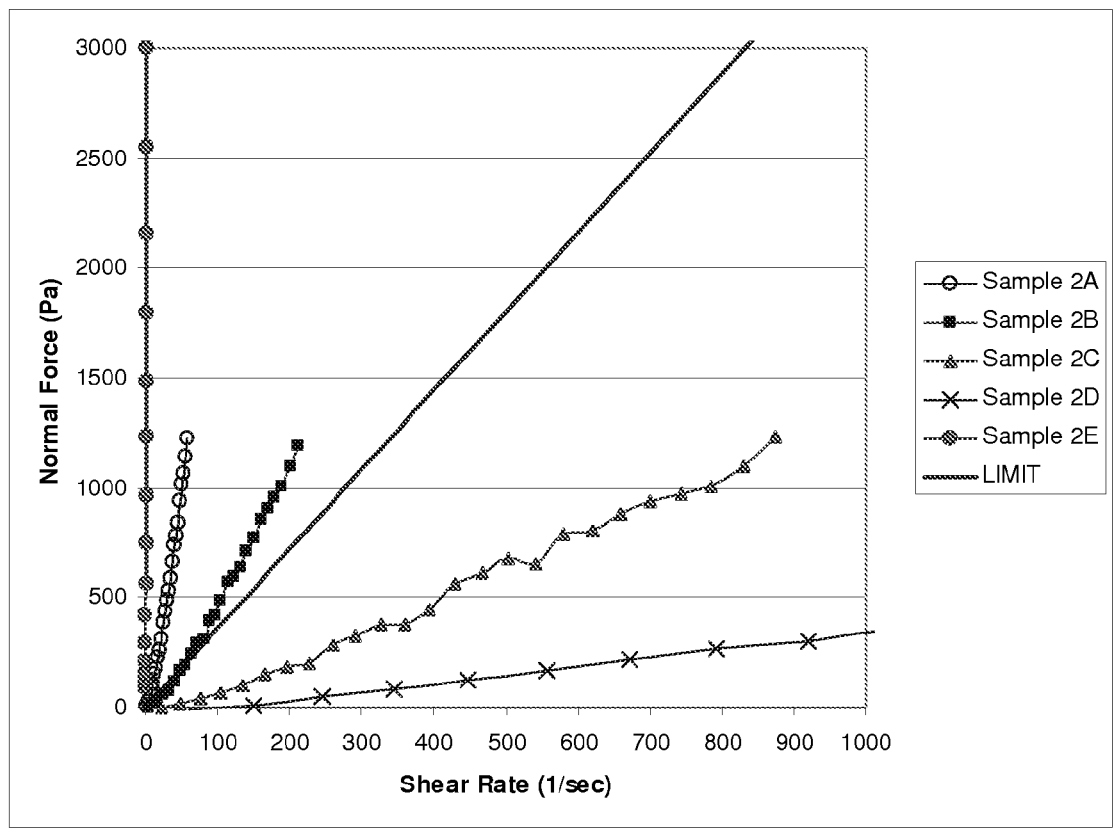
FIG. 2—Normal Force Measurements for Various VBS fluid compositions as detailed in Example 1

FIG. 2 displays a plot of the Normal Stress (Pa) vs Shear Rate (1/sec) for each silicone fluid composition measured in this Example using the controlled stress rheometer, as detailed above. Sample 2A is 100% VBS-1. Sample 2B is VBS-1 diluted to 80%. Sample 2C is VBS-1 diluted to 60%. Sample 2D is VBS-2 diluted to 40%. Sample 2E is 100% VBS-2.

Example 3

The pituitous properties of several T and Q branched silicone fluids, prepared were evaluated in this Example. The T and Q branched silicones were prepared by equilibration of linear dimethyl siloxane polymers in solution with different alkoxy silanes using a strong acid catalyst according to the procedures detailed in WO2006/106362 and as detailed below.

Sample 3A: 500 g of linear dimethyl siloxane polymer with a number average molecular weight (Mn) of 2600 g/mol and a weight average molecular weight (Mw) of 4700 g/mol, 500 g of hydrocarbon solvent (Isopar L) and 6.13 g of tetraethylorthosilicate (TEOS) were charged into a reaction vessel. 1 g of phosphonitrosyl chloride was added and the reaction was carried out at 90° C. for 67 minutes under vacuum. At the end of the reaction, the catalyst was neutralized with 0.5 g of a 10% solution of trihexylamine in hydrocarbon solvent.

Sample 3B: 500 g of the same linear dimethyl siloxane polymer used for Sample 3A, 500 g of hydrocarbon solvent (Hydroseal G250H), and 8.13 g of n-octyltriethoxysilane were charged into a reaction vessel. 1 g of phosphonitrosyl chloride was added and the reaction was carried out at 90° C. for 32 minutes under vacuum. At the end of the reaction, the catalyst was neutralized with 0.45 g of a 10% solution of trihexylamine in hydrocarbon solvent.

Sample 3C: 500 g of the same linear dimethyl siloxane polymer used for Sample 3A, 500 g of hydrocarbon solvent (Hydroseal G250H), and 6.13 g of TEOS were charged into a reaction vessel. 2 g of phosphonitrosyl chloride was added the reaction was carried out at 90° C. for 32 minutes under vacuum. At the end of the reaction, the catalyst was neutralized with 0.91 g of a 10% solution of trihexylamine in hydrocarbon solvent Sample 3D: 500 g of the same linear dimethyl siloxane polymer used for Sample 3A, 500 g of hydrocarbon solvent (Hydroseal G250H), and 4.01 g of methyltrimethoxysilane were charged into a reaction vessel. 1 g of phosphonitrosyl chloride was added the reaction was carried out at 90° C. for 32 minutes under vacuum. At the end of the reaction, the catalyst was neutralized with 0.45 g of a 10% solution of trihexylamine in hydrocarbon solvent.

Figure 3:
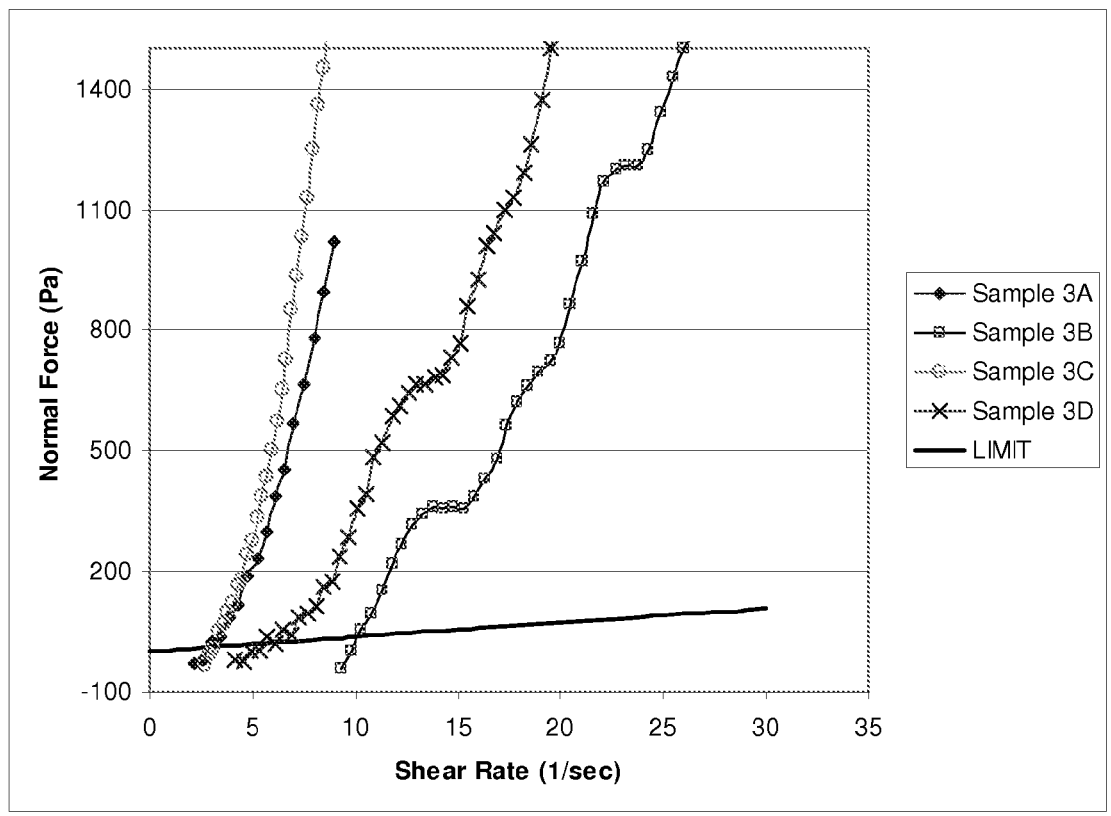
FIG. 3—Normal Force Measurements for Various T and Q branched silicone fluid compositions as detailed in Example 3

FIG. 3 displays a plot of the Normal Stress (Pa) vs Shear Rate (1/sec) for each silicone fluid composition measured in this Example using the controlled stress rheometer, as detailed above.

Example 4

Another series of pituitous silicone fluids were prepared by reacting vinyl-terminated dimethyl siloxane polymers with methylhydrogen cyclics to produce highly branched fluids. In these examples, the stoichiometry of the reaction was controlled so as to produce a highly branched network but yet still below the gel point (the point where the number interconnections between siloxane chains are numerous enough to produce an elastomeric solid).

Several silicone fluid compositions were prepared as detailed below and following the procedures as taught in WO03/093349, WO03/093369, WO2004/058857, and WO2004/58858.

The reaction vessel was charged with the dimethylvinyl-terminated dimethylsiloxane polymer with an average degree of polymerization of ~800 (A) dispersed in a diluent. To this was added the tetramethylcyclotetrasiloxane (B) and the platinum catalyst. The reaction mixture was then heated to 70° C. for three hours resulting in a significant viscosity increase. An additional reactant (C) containing one aliphatic unsaturation was then added in sufficient amount to completely react the remaining SiH functionality. The reaction mixture was again heated to 70° C. for three hours, then allowed to cool and poured from the reaction vessel. The table below summarizes the reactants and amounts used for examples 4A-D.

| Patent Example # | grams of A | Diluent | grams of Diluent | grams of B | SiH:Vi Ratio | Reactant C | grams of C | Product Viscosity[a] |
|---|---|---|---|---|---|---|---|---|
| 4A | 150.0 | Dow Corning ® 200 fluid, 2 cst | 356.6 | 0.77 | 2.60:1 | 1-hexene | 1.32 | 107,000 |
| 4B | 91.2 | Dow Corning ® 200 fluid, 2 cst | 525.7 | 0.44 | 2.40:1 | 1-hexene | 0.82 | 38,000 |
| 4C | 252.0 | Dow Corning ® 200 fluid, 2 cst | 601.4 | 1.28 | 2.58:1 | 1-dodecene | 3.29 | 79,000 |
| 4D | 135.0 | Dow Corning ® 200 fluid, 5 cst | 779.5 | 0.59 | 2.20:1 | 1-dodecene | 1.48 | 58,000 |
| 4E | 123.2 | Isopar ™ L | 711.0 | 0.54 | 2.24:1 | 1-dodecene | 1.28 | 43,000 |
| 4F | 120.6 | Isopar ™ L | 701.9 | 0.54 | 2.30:1 | allyl(EO)$_7$OH[b] | 2.25 | 5,600 |
| 4G | 120.0 | Isopar ™ L | 698.2 | 0.53 | 2.27:1 | allyl(EO)$_7$OH[b] | 2.18 | 122,000 |
| 4H | 286.4 | Dow Corning ® 245 fluid | 1659.8 | 1.49 | 2.65:1 | 1-dodecene | 3.89 | 6400 |
| 4I | 287.4 | Dow Corning ® 200 fluid, 5 cst | 1666.8 | 1.52 | 2.70:1 | 1-dodecene | 4.02 | 4600 |

[a] Measured on Brookfield model RVDV-II+ viscometer, spindle # 7 at 5 rpm.
[b] polyethyleneglycol monoallyl ether with average of 7 (EO) units.

Figure 4:
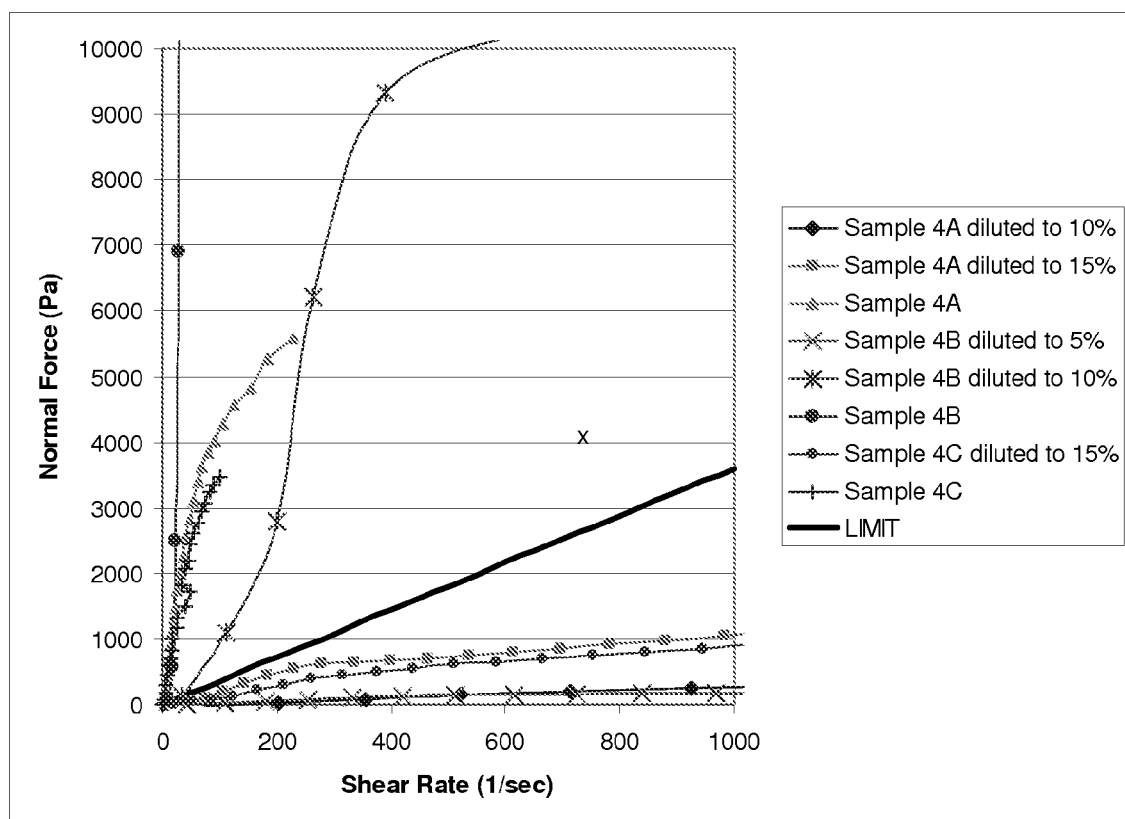
FIG. 4—Normal Force Measurements for Branched silicone fluid compositions as detailed in Example 4

FIG. 4 displays a plot of the Normal Stress (Pa) vs Shear Rate (1/sec) for silicone fluid compositions 4A, 4B, and 4C. Plots for various dilutions of these same samples using the same diluent are also shown in FIG. 4. The dilution percentages in FIG. 4 indicate the percent of polymer in the diluted sample. This data was generated using the controlled stress rheometer, as detailed above.

Figure 5:
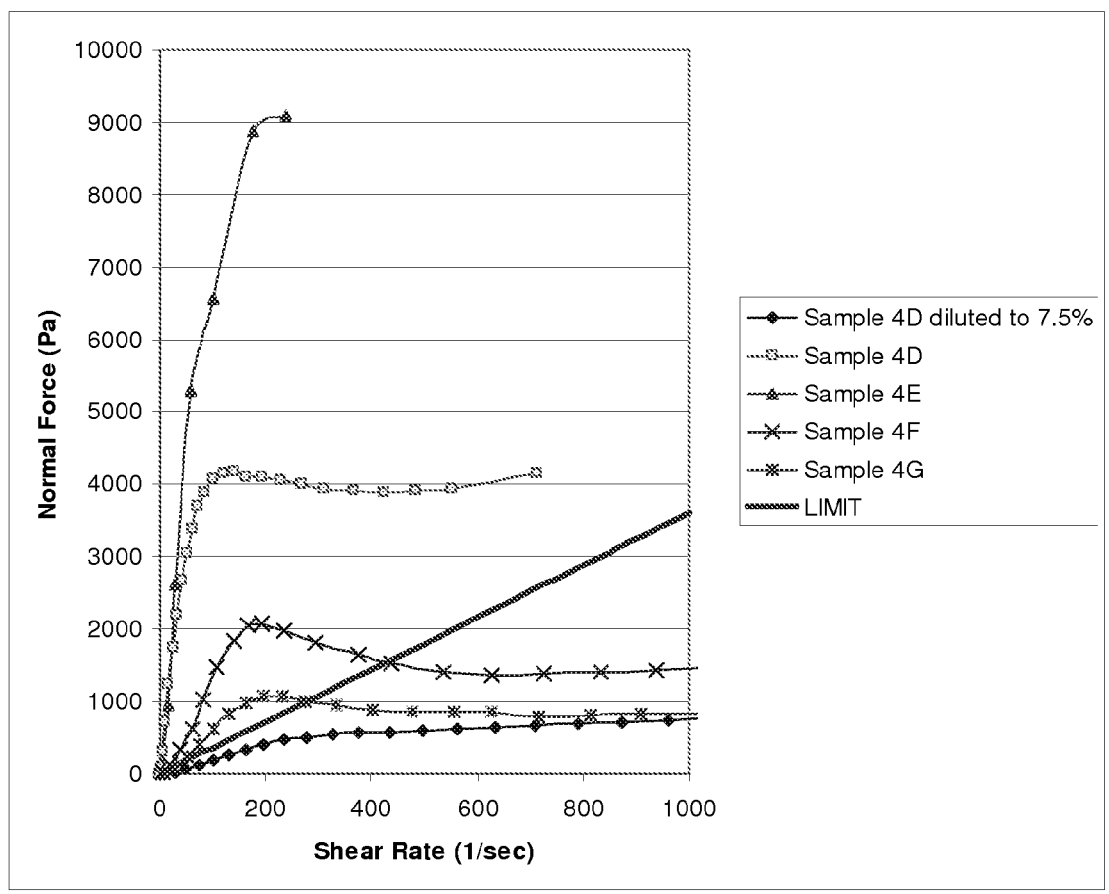
FIG. 5—Normal Force Measurements for Branched silicone fluids as detailed in Example 4

FIG. 5 displays a plot of the Normal Stress (Pa) vs Shear Rate (1/sec) for silicone fluid composition 4D, 4E, 4F, and 4G of this Example using the controlled stress rheometer, as detailed above. FIG. 5 also includes data for Sample 4D that was diluted to 7.5% polymer using the same diluent. The purpose of including data for the diluted samples of this Example is to show that the desired pituitous behavior of the polymer is lost if the concentration of the polymer in the diluent is too low.

Example 5

A series of skin and hair care formulations were prepared as detailed below to demonstrate the benefits of the present silicone fluid compositions.

Moisturizing Lotion

|  | Wt % | INCI name | Trade Name (Supplier) |
|---|---|---|---|
| Part A | | | |
| | 3.20 | Sodium Polyacrylate (and) Dimethicone (and) Cyclopentasiloxane (and) Trideceth-6 (and) PEG/PPG-18/18 Dimethicone | Dow Corning ® RM 2051 Thickening Agent (Dow Corning) |
| | 3.20 | Pituitous siloxane Sample 4E | |
| Part B | | | |
| | 4.30 | Glycerin | |
| | 89.10 | Water | |
| | 0.20 | Propylene Glycol (and) Diazolidinyl Urea (and) Iodopropynyl Carbamate | Liquid Germall ® Plus (Sutton Laboratories) |

Procedure: Mix the ingredients for Part A in a mixing vessel that is large enough to hold the entire batch. Combine the ingredients for Part B in a separate mixing vessel and stir until a homogeneous solution is obtained. Add Part B to Part A in small increments (~5% of total) and mix thoroughly after each addition. When ~30% of Part B has been added and the emulsion is beginning to form, add Part B in larger increments until all of Part B has been added. Continue mixing for 10-15 minutes.

Moisturizing Lotion

Comparative Example

|  | Wt % | INCI name | Trade Name (Supplier) |
|---|---|---|---|
| Part A | | | |
| | 3.20 | Sodium Polyacrylate (and) Dimethicone (and) Cyclopentasiloxane (and) Trideceth-6 (and) PEG/PPG-18/18 Dimethicone | Dow Corning ® RM 2051 Thickening Agent (Dow Corning) |
| | 3.20 | C11-13 Isoparaffin (and) Isohexadecane (and) Dimethiconol | 15% Dow Corning ® SGM 36, 42.5% Isopar L (Exxon), 42.5% Permethyl 101A (Presperse, Inc.) |
| Part B | | | |
| | 4.30 | Glycerin | |
| | 89.10 | Water | |
| | 0.20 | Propylene Glycol (and) Diazolidinyl Urea (and) Iodopropynyl Carbamate | Liquid Germall ® Plus (Sutton Laboratories) |

Procedure: Mix the ingredients for Part A in a mixing vessel that is large enough to hold the entire batch. Combine the ingredients for Part B in a separate mixing vessel and stir until a homogeneous solution is obtained. Add Part B to Part A in small increments (~5% of total) and mix thoroughly after each addition. When ~30% of Part B has been added and the emulsion is beginning to form, add Part B in larger increments until all of Part B has been added. Continue mixing for 10-15 minutes.

These simple moisturizing lotions were compared for sensory characteristics by applying a small amount of the first lotion to the back of one hand and a similar amount of the other lotion to the back of the other hand. Both lotions were rubbed in and the skin feel was judged at three different stages: 1) during rub-in, 2) as the lotion begins to dry on the skin, and 3) after the lotion has completely dried. During rub-in, the lotions had a similar feel. As the lotions were drying, the lotion with the pituitous siloxane felt slightly stickier. The difference between the lotions was quite noticeable after they had dried completely. The lotion with SGM-36 had a powdery, silky skin feel, while the lotion with pituitous siloxane produced a slightly waxy feel on the skin.

Sunscreen Lotion

|  | Wt % | INCI name | Trade Name (Supplier) |
|---|---|---|---|
| Part A | | | |
| | 4.00 | Sodium Polyacrylate (and) Dimethicone (and) Cyclopentasiloxane (and) Trideceth-6 (and) PEG/PPG-18/18 Dimethicone | Dow Corning ® RM 2051 Thcikening Agent (Dow Corning) |
| | 4.00 | Pituitous siloxane Sample 4E | |
| | 7.50 | Octinoxate | |
| | 5.00 | Octisalate | |
| Part B | | | |
| | 4.30 | Glycerin | |
| | 75.00 | Water | |
| | 0.20 | Propylene Glycol (and) Diazolidinyl Urea (and) Iodopropynyl Carbamate | Liquid Germall ® Plus (Sutton Laboratories) |

Procedure: Mix the ingredients for Part A in a mixing vessel that is large enough to hold the entire batch. Combine the ingredients for Part B in a separate mixing vessel and stir until a homogeneous solution is obtained. Add Part B to Part A in small increments (~5% of total) and mix thoroughly after each addition. When ~30% of Part B has been added and the emulsion is beginning to form, add Part B in larger increments until all of Part B has been added. Continue mixing for 10-15 minutes.

Sunscreen Lotion

Comparative Example

|  | Wt % | INCI name | Trade Name (Supplier) |
|---|---|---|---|
| Part A | | | |
| | 4.00 | Sodium Polyacrylate (and) Dimethicone (and) Cyclopentasiloxane (and) Trideceth-6 (and) PEG/PPG-18/18 Dimethicone | Dow Corning ® RM 2051 Thcikening Agent (Dow Corning) |
| | 4.00 | C11-13 Isoparaffin (and) Isohexadecane (and) Dimethiconol | 15% Dow Corning ® SGM 36, 42.5% Isopar L (Exxon), 42.5% Permethyl 101A (Presperse, Inc.) |
| | 7.50 | Octinoxate | |
| | 5.00 | Octisalate | |
| Part B | | | |
| | 4.30 | Glycerin | |
| | 75.00 | Water | |
| | 0.20 | Propylene Glycol (and) Diazolidinyl Urea (and) Iodopropynyl Carbamate | Liquid Germall ® Plus (Sutton Laboratories) |

Procedure: Mix the ingredients for Part A in a mixing vessel that is large enough to hold the entire batch. Combine the ingredients for Part B in a separate mixing vessel and stir until a homogeneous solution is obtained. Add Part B to Part A in small increments (~5% of total) and mix thoroughly after each addition. When ~30% of Part B has been added and the emulsion is beginning to form, add Part B in larger increments until all of Part B has been added. Continue mixing for 10-15 minutes.

The two sunscreens were evaluated for sensory characteristics by the method given above. There was little difference between the two sunscreen lotions during the rub-in and drying stages of the evaluation. After both sunscreen lotions had dried completely, the sunscreen lotion with the silicone gum (SGM 36) had a more powdery, silky feel than the sunscreen lotion with the pituitous siloxane. Both formulations were tested for UVA protection by performing a laboratory test to estimate the SPF (sunburn protection factor). SPF performance is affected by the type of UVA absorbers used and their concentration in the formulation. SPF is also affected by the uniformity of the film left after the formulation dries on the substrate. The SPF for the sunscreen with the pituitous siloxane was 11.0 while the SPF for the sunscreen with the silicone gum was 4.5. Evidently, the pituitous siloxane facilitated the formation of a more uniform film.

Sunscreen Cream with Titanium Dioxide

|        | Wt % | INCI name | Trade Name (Supplier) |
|---|---|---|---|
| Part A | | | |
|        | 2.00 | Lauryl PEG/PPG-18/18 Methicone | Dow Corning ® 5200 Formulation Aid (Dow Corning) |
|        | 1.00 | Stearyl Dimethicone | Dow Corning ® 2503 Cosmetic Wax |
|        | 3.00 | Avobenzone | Escalol 517 (International Specialty Products) |
|        | 5.00 | Octisalate | Escalol 587 (International Specialty Products) |
|        | 8.00 | Pituitous siloxane Sample 4E | |
| Part B | | | |
|        | 2.00 | Titanium Dioxide (and) Triethoxycaprylysilane (and) Alumina | UV-TITAN M265 (Sachleben) |
|        | 3.00 | Phenyl Trimethicone | Dow Corning ® 556 Cosmetic Fluid (Dow Corning) |
| Part C | | | |
|        | 72.40 | Water | |
|        | 0.40 | Sodium Hydroxide | |
|        | 3.00 | Ensulizole | Neo Heliopan Hydro (Symrise) |
|        | 0.20 | Polysorbate 20 | Tween 20 (Croda, Inc.) |

Procedure: Combine the ingredients for Part A into a mixing vessel that is large enough to hold the entire batch. Heat Part A to 55° C. and mix until the Avobenzone has dissolved and the waxes have melted. In a separate vessel disperse the titanium dioxide into the phenyl trimethicone using a high shear mixer to form a homogeneous dispersion, and then add to Part A. In a third mixing vessel, load the ingredients for Part C in the order listed. Make sure that the sodium hydroxide is fully dissolved before adding the ensulizole. Mix Part C until the ensulizole dissolves in the sodium hydroxide solution and the Polysorbate-20 is completely dispersed. Heat Part C to 55° C. and then slowly add to Parts A & B with turbulent mixing. The mixing speed should be sufficient to ensure that Part C is incorporated into the emulsion immediately. After all of Part C has been added, begin cooling the batch to room temperature while continuing to mix at high speed for 10-15 minutes.

Sunscreen Cream with Titanium Dioxide—Comparative Example

|        | Wt % | INCI name | Trade Name (Supplier) |
|---|---|---|---|
| Part A | | | |
|        | 2.00 | Lauryl PEG/PPG-18/18 Methicone | Dow Corning ® 5200 Formulation Aid (Dow Corning) |
|        | 1.00 | Stearyl Dimethicone | Dow Corning ® 2503 Cosmetic Wax (Dow Corning) |
|        | 3.00 | Avobenzone | Escalol 517 (International Specialty Products) |
|        | 5.00 | Octisalate | Escalol 587 (International Specialty Products) |

-continued

| Wt % | INCI name | Trade Name (Supplier) |
|---|---|---|
| Part B | | |
| 8.00 | C11-13 Isoparaffin (and) Dimethiconol (and) Isohexadecane (and) Dimethicone | Dow Corning ® CB-1502 Fluid (Dow Corning) |
| 2.00 | Titanium Dioxide (and) Triethoxycaprylysilane (and) Alumina | UV-TITAN M265 (Sachleben) |
| 3.00 | Phenyl Trimethicone | Dow Corning ® 556 Cosmetic Fluid (Dow Corning) |
| Part C | | |
| 72.40 | Water | |
| 0.40 | Sodium Hydroxide | |
| 3.00 | Ensulizole | Neo Heliopan Hydro (Symrise) |
| 0.20 | Polysorbate 20 | Tween 20 (Croda, Inc.) |

Procedure: See above

The two sunscreen creams have similar esthetics, but the sunscreen cream with the pituitous siloxane produced better UV protection performance. When tested for SPF in-vitro, the sunscreen cream with the pituitous siloxane gave an SPF of 35.6 while the sunscreen cream with CB-1502 gave an SPF of 32.3.

Liquid Foundation

| Wt % | INCI name | Trade Name (Supplier) |
|---|---|---|
| Part A | | |
| 16.50 | Dimethicone | Dow Corning ® 200 Fluid/2 cSt (Dow Corning) |
| 4.28 | Titanium Dioxide and Triethoxycaprylylsilane | Cardre Titanium Dioxide AS (Cardre) |
| 3.71 | Iron Oxides and Triethoxycaprylylsilane | Cardre Red Iron Oxide AS (Cardre, Inc.) |
| 5.93 | Iron Oxides and Triethoxycaprylylsilane | Cardre Yellow Iron Oxide AS (Cardre, Inc.) |
| 2.33 | Iron Oxides and Triethoxycaprylylsilane | Cardre Black Iron Oxide AS (Cardre, Inc.) |
| Part B | | |
| 7.50 | Cyclopentasiloxane (and) PEG/PPG-18/18 Dimethicone | Dow Corning ® 5225C Formulation Aid (Dow Corning) |
| 4.00 | Example Fluid 4A diluted to 13.5% polymer with Dow Corning ® 200 Fluid/2 cSt | |
| Part C | | |
| 54.80 | Water | |
| 1.00 | Sodium Chloride | |
| 0.20 | Polysorbate 20 | Tween 20 (Croda, Inc.) |

PROCEDURE: Prepare Part A by combing the pigment powders with the dimethicone and then mixing at high speed with a mixing blade designed for dispersing solids into liquid (e.g. a Cowles Blade). Combine Part A with the ingredients in Part B in a mixing vessel that is large enough to accommodate the entire batch. Combine the ingredients for Part C in a separate vessel and stir until the salt is completely dissolved. Add Part C to Parts A and B while stirring to provide strong turbulent mixing. As Part C is added, the emulsion will thicken. After all of Part C has been added, continue mixing for 10-15 minutes.

Liquid Foundation

| Wt % | INCI name | Trade Name (Supplier) |
|---|---|---|
| Part A | | |
| 16.50 | Dimethicone | Dow Corning ® 200 Fluid/2 cSt (Dow Corning) |
| 4.28 | Titanium Dioxide and Triethoxycaprylylsilane | Cardre Titanium Dioxide AS (Cardre) |
| 3.71 | Iron Oxides and Triethoxycaprylylsilane | Cardre Red Iron Oxide AS (Cardre, Inc.) |
| 5.93 | Iron Oxides and Triethoxycaprylylsilane | Cardre Yellow Iron Oxide AS (Cardre, Inc.) |
| 2.33 | Iron Oxides and Triethoxycaprylylsilane | Cardre Black Iron Oxide AS (Cardre, Inc.) |

-continued

| | Wt % | INCI name | Trade Name (Supplier) |
|---|---|---|---|
| Part B | | | |
| | 7.50 | Cyclopentasiloxane (and) PEG/PPG-18/18 Dimethicone | Dow Corning ® 5225C Formulation Aid (Dow Corning) |
| | 4.00 | Example Fluid 4B | |
| Part C | | | |
| | 54.80 | Water | |
| | 1.00 | Sodium Chloride | |
| | 0.20 | Polysorbate 20 | Tween 20 (Croda, Inc.) |

Liquid Foundation

Comparative Example

| | Wt % | INCI name | Trade Name (Supplier) |
|---|---|---|---|
| Part A | | | |
| | 16.50 | Dimethicone | Dow Corning ® 200 Fluid/2 cSt (Dow Corning) |
| | 4.28 | Titanium Dioxide and Triethoxycaprylylsilane | Cardre Titanium Dioxide AS (Cardre) |
| | 3.71 | Iron Oxides and Triethoxycaprylylsilane | Cardre Red Iron Oxide AS (Cardre, Inc.) |
| | 5.93 | Iron Oxides and Triethoxycaprylylsilane | Cardre Yellow Iron Oxide AS (Cardre, Inc.) |
| | 2.33 | Iron Oxides and Triethoxycaprylylsilane | Cardre Black Iron Oxide AS (Cardre, Inc.) |
| Part B | | | |
| | 7.50 | Cyclopentasiloxane (and) PEG/PPG-18/18 Dimethicone | Dow Corning ® 5225C Formulation Aid (Dow Corning) |
| | 4.00 | Cyclopentasiloxane (and) Trimethylsiloxysilicate | Dow Corning ® 749 Fluid |
| Part C | | | |
| | 54.80 | Water | |
| | 1.00 | Sodium Chloride | |
| | 0.20 | Polysorbate 20 | Tween 20 (Croda, Inc.) |

PROCEDURE: Prepare Part A by combing the pigment powders with the dimethicone and then mixing at high speed with a mixing blade designed for dispersing solids into liquid (e.g. a Cowles Blade). Combine Part A with the ingredients in Part B in a mixing vessel that is large enough to accommodate the entire batch. Combine the ingredients for Part C in a separate vessel and stir until the salt is completely dissolved. Add Part C to Parts A and B while stirring to provide strong turbulent mixing. As Part C is added, the emulsion will thicken. After all of Part C has been added, continue mixing for 10-15 minutes.

The liquid foundations made with the pituitous siloxane 4A diluted to 13.5% polymer and with pituitous siloxanes 4B had a smoother texture and a higher viscosity than the comparative example formulation made with Dow Corning® 749 Fluid. When measured using a Brookfield rotational viscometer equipped with a #91T-spindle at a speed of 50 rpm, the liquid foundation made with pituitous siloxane 4A diluted to 13.5% polymer had a viscosity of approximately 1,900 cP. The liquid foundation made with pituitous siloxane 4B had a viscosity of approximately 4,300 cP at 50 rpm. The liquid foundation made with Dow Corning® 749 Fluid had a viscosity had to be measured at 100 rpm due to its lower viscosity and the viscosity was approximately 450 cP.

Rinse-Off Hair Conditioner

| | Wt % | INCI name | Trade Name (Supplier) |
|---|---|---|---|
| Part A | | | |
| | 1.50 | Hydroxyethyl Cellulose | Natrosol 250HHR (Hercules, Inc.) |
| | 3.20 | Water | |
| Part B | | | |
| | 1.00 | Cetearyl Alcohol | Crodacol CS-50 (Croda, Inc.) |
| | 1.00 | PEG-100 Stearate (and) Glyceryl Stearate | Arlacel 165 (Croda, Inc.) |
| Part C | | | |
| | 2.00 | Example Fluid 4E in Isopar L) | |
| Part D | | | |
| | 0.30 | Cetrimonium Chloride | Arquad 16-29W (Akzo Nobel Chemicals Inc.) |
| | 0.20 | DM DM Hydantoin | Glydant (Lonza) |
| | q.s. | Water | |

Rinse-Off Hair Conditioner

|  | Wt % | INCI name | Trade Name (Supplier) |
|---|---|---|---|
| Part A | | | |
| | 1.50 | Hydroxyethyl Cellulose | Natrosol 250HHR (Hercules, Inc.) |
| | 3.20 | Water | |
| Part B | | | |
| | 1.00 | Cetearyl Alcohol | Crodacol CS-50 (Croda, Inc.) |
| | 1.00 | PEG-100 Stearate (and) Glyceryl Stearate | Arlacel 165 (Croda, Inc.) |
| Part C | | | |
| | 2.00 | Example Fluid 4F in Isopar L | |
| Part D | | | |
| | 0.30 | Cetrimonium Chloride | Arquad 16-29W (Akzo Nobel Chemicals Inc.) |
| | 0.20 | DM DM Hydantoin | Glydant (Lonza) |
| | q.s. | Water | |

Procedure:
Prepare part A by sifting the hydroxyethyl cellulose into the water and stir until fully dispersed (the mixture will be hazy). Heat Part A to ~70° C. and mix until the mixture clears. Add the ingredients for Part B into Part A while Part A is still hot (60-70° C.). When the solid ingredients are melted and dispersed, mix for another 5 minutes and then allow the mixture to cool. Increase the mixer speed as the batch cools and thickens to maintain turnover. When the batch reaches 40° C., add Part C and mix vigorously to disperse the siloxane fluid. Add the ingredients for Part D and continue mixing until the batch reaches room temperature. The amount of water in Part D is determined by checking the weight of the batch after it cools below 250 C and restoring the weight of water lost by evaporation.

Evaluation:
To evaluate the hair conditioning effect of the above compositions, the compositions were applied to human hair tresses by following the procedure below:
Slightly bleached European human hair from International Hair Importer and Products Inc. is used in a combing evaluation protocol for testing the conditioners. A master hand of hair eight inches in length is subdivided into a series of individual hair tresses. Each tress weighed 2.5 grams. A ½ inch of the root end of the hair was trimmed and glued to a 2"×2" plastic tab using DUCO CEMENT®. The cement is allowed to dry over night, and the hair tress is combed and trimmed to a length so that six inches of hair extends below the bottom of the plastic tab. A hole is punched in the middle of the tab ¼" from the top. Each tress is rinsed for 15 seconds under 40° C. tap water. Using a pipette, 1.0 g of a 9% Sodium Lauryl Sulfate (active) solution is applied and lathered through the tress for 30 seconds. The tress is rinsed for 30 seconds under running water. Excess water is removed from the tress by passing the tress between the index and middle fingers. The test conditioner is applied to the tress in the amount of 0.8 g and the conditioner was worked into the tress with the fingers for 30 seconds. The tress is rinsed for 30 seconds under tap water at 40° C. The excess water is removed by pulling the tresses through the index and middle fingers. The tresses are allowed to dry separately on a paper towel, overnight at ambient conditions.
The hair treated with the example conditioners had a smooth feel when wet but were not slimy. After drying, both treated tresses had a smooth, soft feel.

Curl Retention Testing
Sensory evaluation of the pituitous siloxane fluids has indicated that films of these fluids can be somewhat tacky. In order to determine if this film property correlates with curl retention on hair, a simple screening test was performed. Small swatches (2 g) of natural virgin brown human hair were washed in a dilute solution of sodium lauryl sulfate, rinsed, and then pulled between the fingers to remove excess water. Then, 100 μL of the test material was applied evenly along the length of the hair swatch and a comb was passed through the swatch to help distribute the test material and to detangle the swatch. The swatch was wound around a spiral plastic curling rod and allowed to dry overnight in a 40° C. oven. The swatches were then placed in a controlled humidity chamber set at 70% relative humidity and 25° C. At various time intervals, the length of the swatches was measured. The percent curl retention is calculated as follows:

$$\% \text{ curl retention} = (L_{max} - L_T)/(L_{max} - L_{T=0}) \times 100$$

where
$L_{max}$=un-curled length of swatch
$L_T$=swatch length after a certain time in the chamber
$L_{T=0}$=swatch length at the start of the test The following materials were tested. Duplicate swatches for each treatment were tested and the curl retention values averaged:
1) Deionized water (control)
2) Isopar L (solvent blank)
3) Pituitous Fluid from example 4E diluted to 2% polymer with Isopar L
4) Pituitous Fluid from example 4G diluted to 2% polymer with Isopar L
5) Pituitous Fluid from example 6D diluted to 2% polymer with Isopar L The following table shows the curl retention results for the five treatments. The results indicate that the pituitous siloxanes provide better curl retention than water and the solvent blank. During the evaluation, it was noted that the swatches treated with the pituitous siloxanes had a soft, slippery feel and that the curl definition was better than either the water or solvent-treated swatches. Curl definition refers to the appearance of the swatches after they had been in the controlled humidity chamber for several hours. Better curl definition corresponds to the tendency of the swatches to hold a compact shape, independent of the length of the swatch.

Treatment

| Time (min) | 1 | 2 | 3 | 4 | 5 |
|---|---|---|---|---|---|
| 0 | 100.0 | 100.0 | 100.0 | 100.0 | 100.0 |
| 15 | 39.3 | 47.7 | 63.4 | 73.1 | 73.1 |
| 30 | 31.3 | 39.7 | 51.9 | 63.8 | 67.7 |
| 60 | 29.6 | 32.6 | 46.7 | 62.7 | 66.5 |
| 90 | 27.8 | 32.6 | 46.7 | 60.6 | 62.0 |
| 120 | 27.8 | 32.6 | 44.6 | 60.6 | 62.0 |
| 240 | 26.1 | 32.6 | 44.6 | 57.5 | 61.0 |
| 300 | 26.1 | 32.6 | 44.6 | 57.5 | 61.0 |

Example 6

Another series of pituitous silicone fluids were prepared by reacting vinyl-terminated dimethyl siloxane polymers with methylhydrogen cyclics to produce highly branched fluids. In these examples, the stoichiometry of the reaction was controlled so as to produce a highly branched network but yet still below the gel point (the point where the number interconnections between siloxane chains are numerous enough to produce an elastomeric solid). The reaction vessel was charged with the dimethylvinyl-terminated dimethylsiloxane polymer (A) with an average degree of polymerization of ~4800 and a % vinyl level of ~150 ppm ($C_2H_3$) dispersed in Isopar™L diluent. To this was added the tetramethylcyclotetrasiloxane (B) followed by platinum catalyst (C) diluted in dimethylvinyl-terminated dimethylsiloxane with a vinyl level of 2.2% ($C_2H_3$). The reaction mixture was then heated to 85 C for 18 hours resulting in a significant viscosity increase. The reaction mixture was then allowed to cool and poured from the reaction vessel. The table below summarizes the reactants and amounts used for examples 6A, B, C, D, and E.

| Patent Example # | grams of A | grams of Diluent | milligrams of B | Wt. Ratio g of A/ mg of B | grams of C | Product Viscosity (cps)[a] |
|---|---|---|---|---|---|---|
| 6A | 2.00 | 38.17 | 1.39 | 1.44 | 0.015 | 64 |
| 6B | 2.00 | 38.17 | 1.50 | 1.33 | 0.015 | 200 |
| 6C | 2.00 | 38.17 | 1.61 | 1.25 | 0.015 | 460 |
| 6D | 25.00 | 477.12 | 20.21 | 1.24 | 0.19 | 1200 |
| 6E | 2.00 | 38.17 | 1.67 | 1.20 | 0.015 | 10000 |

[a]Measured on Brookfield model RVDV-II+ viscometer, LV spindle # 2 at 20 rpm.

Figure 6:
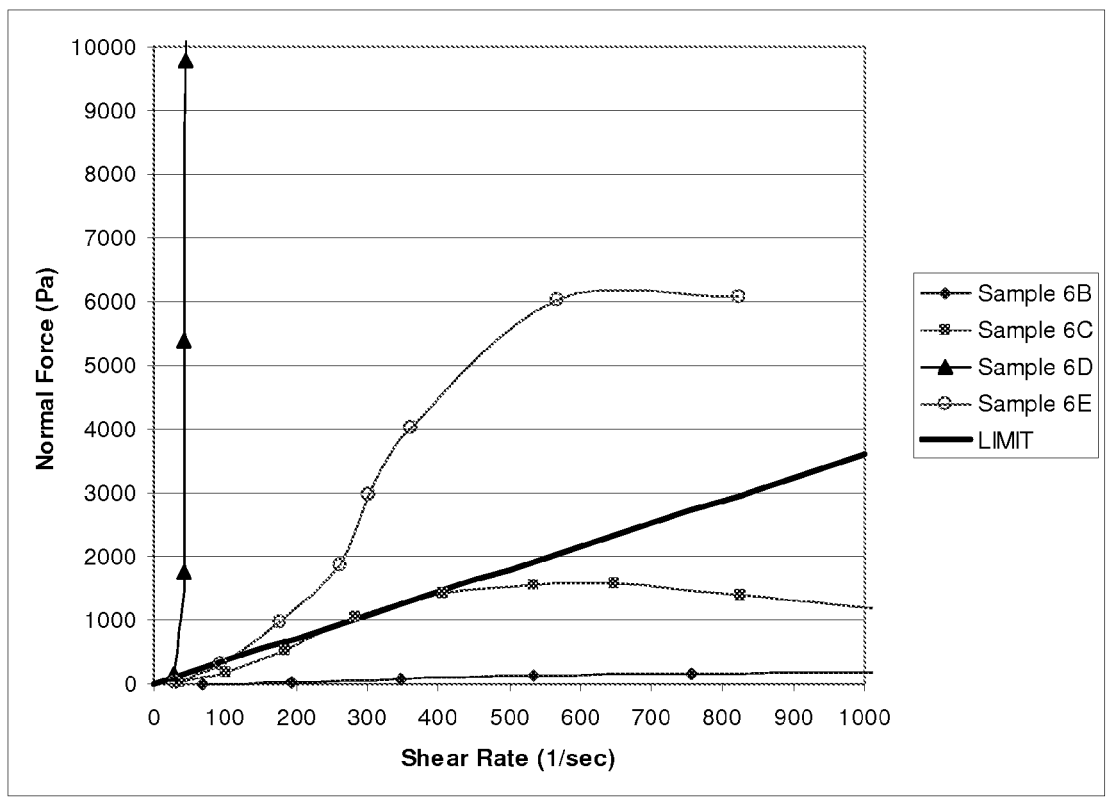
FIG. 6—Normal Force Measurements for Branched silicone fluids as detailed in Example 6

FIG. 6 displays a plot of the Normal Stress (Pa) vs Shear Rate (1/sec) for silicone fluid compositions 6B through 6E of this Example using the controlled stress rheometer, as detailed above. Sample 6A was not tested on the rheometer because it did not exhibit the stringing behavior of a pituitous fluid.

Example 7

Figure 7:
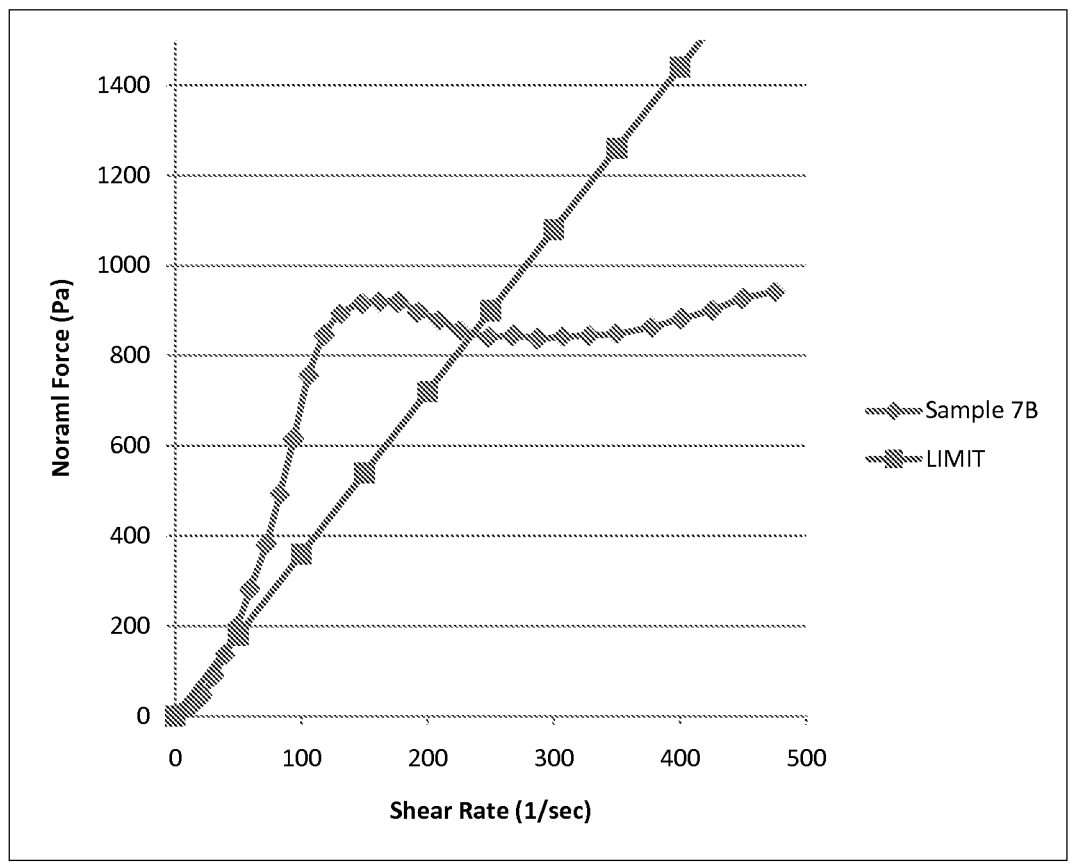
FIG. 7—Normal Force Measurements for Branched silicone fluids as detailed in Example 7B

The reaction vessel was charged with the dimethylvinylsiloxy-terminated dimethylsiloxane polymer with an average degree of polymerization of ~800 (A) dispersed in toluene. To this was added an SiH functional crosslinker (as indicated in the table below) and the platinum catalyst. The reaction mixture was then heated to 70° C. for three hours resulting in a significant viscosity increase. 1-hexene was then added in sufficient amount to completely react the remaining SiH functionality. The reaction mixture was again heated to 70° C. for three hours, then allowed to cool and poured from the reaction vessel. A second diluent, Dow Corning® 200 fluid, 5 cst, was then added to the reaction product solution and the toluene was stripped off under vacuum using a roto-evaporator. The table below summarizes the reactants and amounts used for examples 7A and B. FIG. 7 displays a plot of the Normal Stress (Pa) vs Shear Rate (1/sec) for silicone fluid compositions 7B using the controlled stress rheometer, as detailed above.

| Patent Example # | grams of A | Crosslinker | grams of Crosslinker | SiH:Vi Ratio | grams of 1-hexene | grams of Dow Corning® 200 fluid, 5 cst | Product Viscosity[a] |
|---|---|---|---|---|---|---|---|
| 7A | 106.85 | tetramethylcyclo tetrasiloxane | 0.619 | 2.95:1 | 3.23 | 967.2 | 4800 |
| 7B | 57.99 | Dimethyl methylhydrogen copolymer[b] | 6.446 | 26.6:1 | 26.03 | 365.1 | 3200 |

[a]Measured on Brookfield model RVDV-II+ viscometer, spindle # 7 at 5 rpm.
[b]A trimethylsiloxy terminated dimethyl, methylhydrogen siloxane copolymer with an average degree of polymerization of ~10 and an average of ~5 methylhydrogen siloxane groups.

Example 8

A series of emulsions were prepared as detailed below to demonstrate the pituitous silicone fluids may be provided in a water based emulsion.

Example 8A

First, 10.4 g of pituitous siloxane (Example 4H), 0.4 g of C12-13 Pareth-4 (BRIJ™ LT4) and 0.43 g of C12-13 Pareth-23 (BRIJ™ 35) were successively poured in an appropriate cup and then mix for 25 s at 3500 rpm. Then, 1.02 g of distilled water was added to the oil mixture and mixed for 25 s at 3500 rpm. A concentrated oil in water emulsion formed which was further diluted by adding a small fraction of distillated water until a 50% of silicone content was reached. Mean particle size of the emulsion was approximately 0.774 μm.

Example 8B

First, 10.4 g of pituitous siloxane (Example 41), 0.38 g of C12-13 Pareth-4 (BRIJ™ LT4) and 0.45 g of C12-13 Pareth-23 (BRIJ™ 35) were successively poured in an appropriate cup and then mix for 25 s at 3500 rpm. Then, 0.7 g of distillated water was then added to the oil mixture and mixed for 25 s at 3500 rpm. A concentrated oil in water formed which was further diluted by adding a small fraction of distillated water until a 50% of silicone content was reached. Mean particle size of the emulsion was approximately 0.664 μm.

Example 8C

First, 23.8 g of pituitous siloxane (Example 7A), 0.64 g of C11-C14 isoalcohols, C13-rich, ethoxylated (Renex 30) and 4.4 g of Sodium (C14-16) olefin sulfonate (Bioterge AS-40) were successively poured in an appropriate cup and then mixed for 25 s at 3500 rpm. Then, 2 g of distillated water was added to the oil mixture and mixed for 25 s at 3500 rpm. A concentrated oil in water formed which was further diluted by adding a small fraction of distillated water until a 54% of silicone content was reached. Mean particle size of the emulsion was approximately 15.2 μm.

The invention claimed is:
1. A personal care composition comprising a silicone fluid having pituitous rheological properties wherein the silicone fluid comprises a highly branched organopolysiloxane prepared by reacting;

a') an organohydrogencyclosiloxane having the formula $[(CH_3)HSiO]_g$ where g is 3 to 8, and b') a vinyl terminated polydimethylsiloxane having the average formula $(CH_2=CH)Me_2SiO(Me_2SiO)_{dp}SiMe_2(CH=CH_2)$ having a degree of polymerization (dp) of 4000 to about 4800, in a carrier fluid and in the presence of a hydrosilylation catalyst where the amount of a') and b') in the reaction is such to provide a molar ratio of vinyl to SiH of 0.9/1 to 1.2/1, and a solids content of at least 5 wt %, wherein the pituitous rheological properties of the silicone fluid are determined from a plot of normal force in Pascals vs a perpendicular shear rate in $\sec^{-1}$ wherein the plot falls above a limit line having the equation y=3.6x where y is the normal force and x is the perpendicular shear rate, and wherein the carrier fluid is a hydrocarbon solvent.

2. The personal care composition according to claim 1, wherein g is 4 to 6.

3. The personal care composition according to claim 1, wherein g is 4.

4. The personal care composition according to claim 1, wherein the molar ratio of vinyl to SiH is 0.95/1 to 1.1/1.

5. The personal care composition according to claim 1, wherein the solids content is at least 10 wt %.

6. The personal care composition according to claim 1, wherein the solids content is at least 20 wt %.

7. The personal care composition according to claim 1, wherein the hydrocarbon solvent comprises an aromatic hydrocarbon solvent or an aliphatic hydrocarbon solvent.

8. The personal care composition according to claim 7, wherein the hydrocarbon solvent comprises a C11-C13 isoparaffin.

9. The personal care composition according to claim 1, wherein the hydrosilylation catalyst is a platinum catalyst.

10. A personal care composition comprising a silicone fluid having pituitous rheological properties wherein the silicone fluid comprises a highly branched organopolysiloxane prepared by reacting;

a') an organohydrogencyclosiloxane having the formula $[(CH_3)HSiO]_g$ where g is 3 to 8, and b') a vinyl terminated polydimethylsiloxane having the average formula $(CH_2=CH)Me_2SiO(Me_2SiO)_{dp}SiMe_2(CH=CH_2)$ having a degree of polymerization (dp) of 4000 to 9000, in a carrier fluid and in the presence of a hydrosilylation catalyst where the amount of a') and b') in the reaction is such to provide a molar ratio of vinyl to SiH of 0.9/1 to 1.2/1, and a solids content of at least 5 wt %, wherein the pituitous rheological properties of the silicone fluid are determined from a plot of normal force in Pascals vs a perpendicular shear rate in $\sec^{-1}$ wherein the plot falls above a limit line having the equation y=3.6x where y is the normal force and x is the perpendicular shear rate, and wherein the carrier fluid is a hydrocarbon solvent.

11. The personal care composition according to claim 10, wherein the dp is 4000 to 6000.

12. The personal care composition according to claim 10, wherein g is 4 to 6.

13. The personal care composition according to claim 10, wherein g is 4.

14. The personal care composition according to claim 10, wherein the molar ratio of vinyl to SiH is 0.95/1 to 1.1/1.

15. The personal care composition according to claim 10, wherein the solids content is at least 10 wt %.

16. The personal care composition according to claim 10, wherein the solids content is at least 20 wt %.

17. The personal care composition according to claim 10, wherein the hydrocarbon solvent comprises an aromatic hydrocarbon solvent or an aliphatic hydrocarbon solvent.

18. The personal care composition according to claim 17, wherein the hydrocarbon solvent comprises a C11-C13 isoparaffin.

19. The personal care composition according to claim 10, wherein the hydrosilylation catalyst is a platinum catalyst.

\* \* \* \* \*